United States Patent [19]  [11] 3,957,480
Kornis  [45] May 18, 1976

[54] ALKYL AND HALOALKYLPYRAZOLES, COMPOSITIONS AND PROCESS
[75] Inventor: Gabriel Kornis, Kalamazoo, Mich.
[73] Assignee: The Upjohn Company, Kalamazoo, Mich.
[22] Filed: Dec. 23, 1974
[21] Appl. No.: 535,360

[52] U.S. Cl. .................................. 71/92; 71/66; 260/247.1 M; 260/247.5 E; 260/293.7; 260/310 R
[51] Int. Cl.² ............ C07D 233/10; C07D 207/10; C07D 211/16; A01N 9/22
[58] Field of Search.............. 260/310, 247.5, 247.1, 260/293.7; 71/92

[56] References Cited
OTHER PUBLICATIONS
Michaelis et al., Chem. Abst., Vol. 4, pp. 2827–2828 (1910).

Primary Examiner—Harry I. Moatz
Attorney, Agent, or Firm—John J. Killinger; Roman Saliwanchik

[57] ABSTRACT
Compounds of the formula:

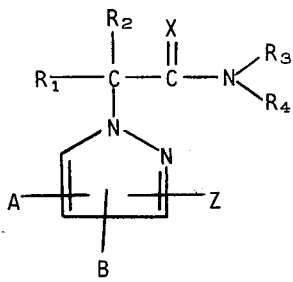

wherein $R_1$ and $R_2$ are the same or different and are hydrogen, alkyl of from 1 to 6 carbon atoms, inclusive, or phenyl; $R_3$ is hydrogen, alkyl of from 1 to 8 carbon atoms, inclusive, phenyl, or benzyl; $R_4$ is hydrogen or alkyl of from 1 to 6 carbon atoms, inclusive, and $R_3$ and $R_4$ can be joined together to form a heterocyclic ring selected from the group consisting of morpholine, pyrrolidine or piperidine; X is oxygen or sulfur; A and B are the same or different, and are hydrogen, alkyl of from 1 to 6 carbon atoms inclusive, cycloalkyl of from 3 to 7 carbon atoms, inclusive, haloalkyl, and halogen; Z is an alkyl group of from 1 to 6 carbon atoms, inclusive, or a cycloalkyl group of from 3 to 7 carbon atoms provided that when A and B are halogen, Z is located at the 4 or 5 positions.

Methods for preparing the compounds, and agricultural compositions comprising the compounds with carriers for use as herbicides by application to foliage, soil or ponds for the control of unwanted vegetation are disclosed.

87 Claims, No Drawings

ALKYL AND HALOALKYLPYRAZOLES, COMPOSITIONS AND PROCESS

BRIEF DESCRIPTION OF THE INVENTION

This invention concerns novel compounds of the Formula I which are useful in the agricultural arts as herbicides. The compounds are formulated with carriers to prepare compositions which can be applied as pre- and post-emergent herbicides.

DETAILED DESCRIPTION OF THE INVENTION

The invention relates to substituted pyrazoles, which are useful in agriculture as herbicides of the formula:

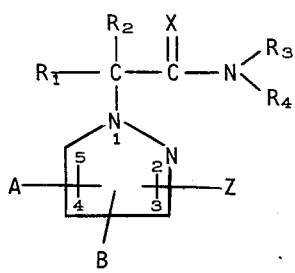

wherein $R_1$ and $R_2$ are the same or different and are selected from the group consisting of hydrogen, alkyl of 1 to 6 carbon atoms, inclusive, or phenyl; $R_3$ is selected from the group consisting of hydrogen, alkyl of from 1 to 8 carbon atoms, inclusive, phenyl or benzyl; $R_4$ is selected from the group consisting of hydrogen or alkyl of from 1 to 6 carbon atoms, inclusive, or together $R_3$ and $R_4$ can be joined to form a heterocyclic ring selected from the group consisting of morpholine, pyrrolidine or piperidine. A and B are the same or different and are selected from the group consisting of hydrogen, alkyl of from 1 to 6 carbon atoms, inclusive, cycloalkyl of from 3 to 7 carbon atoms, inclusive, haloalkyl, and halogen. Z is an alkyl group of from 1 to 6 carbon atoms, inclusive, or a cycloalkyl group of from 3 to 7 carbon atoms provided that when A and B are halogen, Z is located at the 4 or 5 positions.

The preferred compounds, i.e., those having greater biological activity can be represented by the following Formulae II through VI, inclusive. These formulae represent the preferred compounds based upon structure-activity relationships.

Formula II

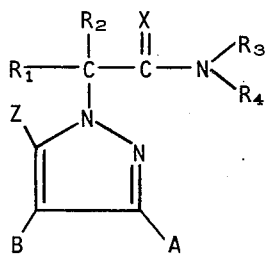

wherein Z is alkyl of from 1 to 3 carbon atoms; $R_1$, $R_2$, $R_3$, $R_4$, X, A and B are as defined for Formula I.

Formula III

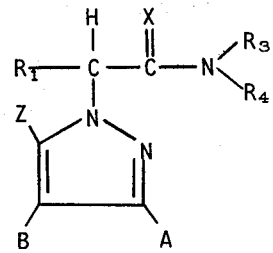

wherein A and B are halogen and Z is alkyl of from 1 to 3 carbon atoms; $R_1$, $R_3$, $R_4$, and X are as defined for Formula I.

Formula IV

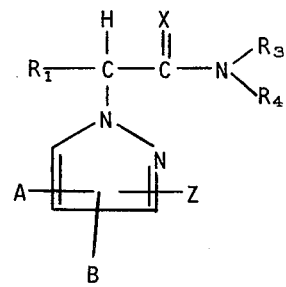

wherein $R_1$ is an alkyl group of from 1 to 3 carbon atoms, inclusive, and $R_3$, $R_4$, X, Z, A and B are as defined for Formula I.

Formula V

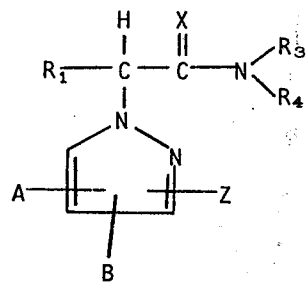

wherein $R_3$ and $R_4$ are methyl or ethyl and $R_1$, X, A, B and Z are as defined for Formula I.

Formula VI

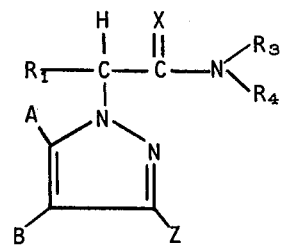

wherein Z is alkyl or cycloalkyl, B is alkyl or halogen, X is oxygen, and A, $R_1$, $R_3$ and $R_4$ are as defined for Formula I.

The term alkyl of 1 to 6 carbon atoms, or 1 to 8, inclusive, denotes a straight or branched chain hydrocarbon group as exemplified by methyl, ethyl, propyl, isopropyl, butyl, isobutyl, tertiary butyl, pentyl, isopentyl, 3-methylbutyl, isohexyl, 2-methylpentyl, 3-methylpentyl, heptyl, octyl and the like.

Haloalkyl includes the term alkyl as defined above, for example chloromethyl, dichloromethyl, trifluoromethyl, 2-chloropropyl, 3-chloropropyl and the like.

a 2-haloalkanoate ester with the appropriately substituted pyrazole in the presence of sodium or potassium carbonate and acetone. Other bases and solvents may be used, for example sodium ethoxide in ethanol, sodium hydride in toluene or tetrahydrofuran, and so on. The temperature may vary from 30° C. to the refluxing temperature of the solvent.

The second step is base hydrolysis of the ester to the acid, followed by activation to the acid chloride and treatment with an amine to furnish the desired amide.

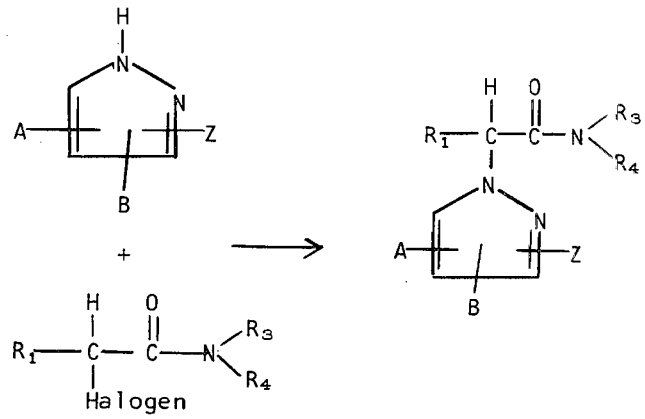

Process B

Cycloalkyl of 3 to 6 carbon atoms is exemplified by cyclopropyl, cyclobutyl, cyclopentyl, and cyclohexyl.

Halogen is exemplified by bromine and chlorine. The compounds of Formulae I, II, III, IV, V, VI are prepared according to processes illustrated by the following reaction schemes:

wherein $R_1$, $R_3$, $R_4$, A, B, and Z are as previously described.

The process is carried out by reacting an appropriately substituded pyrazole with a previously synthesized 2-haloalkanoamide in the presence of base, such as sodium hydroxide, sodium hydride, sodium ethox-

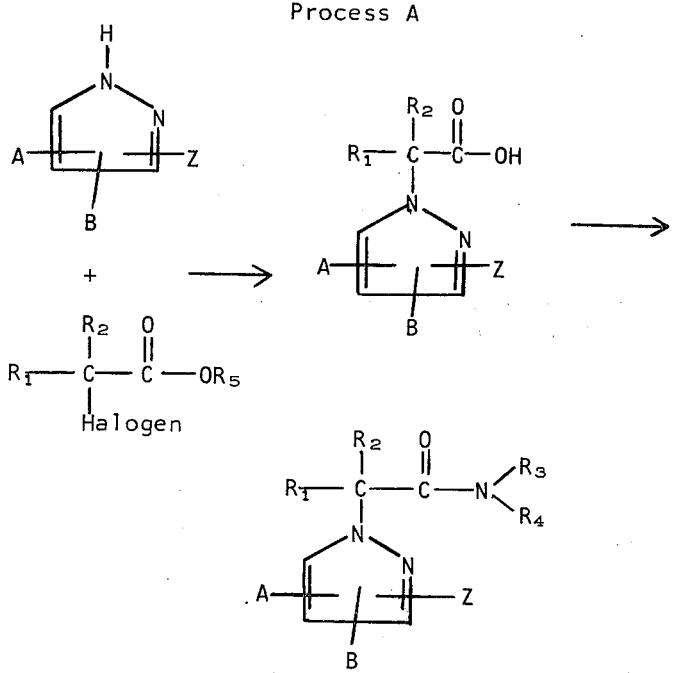

Process A wherein A, B, Z, $R_1$, $R_2$, $R_3$, and $R_4$ are defined as above and $R_5$ is an alkyl group of 1 to 6 carbon atoms.

The first step in this process involves the reaction of ide, potassium carbonate and the like. Useful solvents are toluene, benzene, alcohols, water and the like. The reaction proceeds between room temperature and the refluxing temperature of the solvent. In some cases, the reaction proceeds in the absence of any solvent, between temperatures of 100 and 160° C.

The desired compound is isolated and purified by conventional means such as crystallization or distillation. In a number of cases isomer formation takes place at the 3 and 5 positions and separation can be effected by column chromatography.

Process C

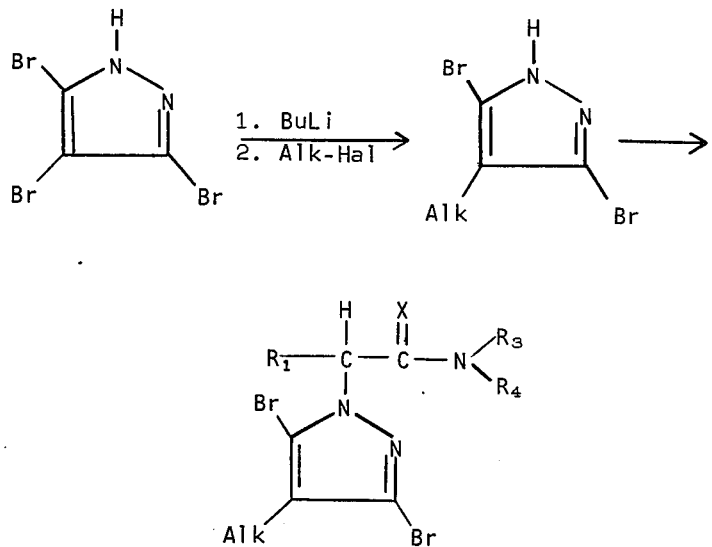

wherein $R_1$, $R_3$, $R_4$, and X are as previously described.

The process is carried out by treating tribromopyrazole with butyl lithium at low temperature in the presence of an inert gas. Addition of an alkyl iodide and workup in the usual manner yields 3,5-dibromo-4-alkylpyrazole which then is reacted further according to processes A or B to yield the desired pyrazole amides.

Process D

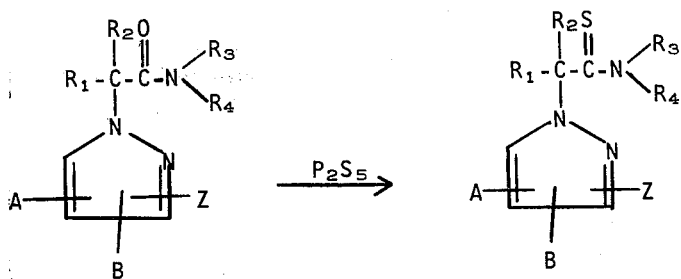

wherein $R_1$, $R_2$, $R_3$, $R_4$, A, B, and Z are as previously described.

The process is carried out by reacting a pyrazole amide with phosphorous pentasulfide in the presence of pyridine, xylene, toluene and the like and heating the stirred reaction mixture for a period of time. Isolation of the product is carried out in the conventional way, such as pouring into water and purifying by recrystallization or column chromatography.

The compounds of the Formula I of this invention have been found to be active as herbicides both pre- and post-emergent. The compounds of the Formula I can be used to prevent damage to field crops due to weed competition, and they can be used to prevent unsightly and deleterious growths of weeds on home lawns, golf courses, cemeteries, railroad rights-of-way, and parks.

Compounds of the Formula I have been found to be highly active against both broadleaf and grassy weeds. illustratively, against various weeds, e.g., crabgrass (*Digitaria sanguinalis L.*), yellow foxtail (*Setaria glauca L.*), wild oats (*Avena fatua L.*), bindweed (*Convolvulus arvensis L.*), Johnson grass (*Sorghum halepense L.*), buckhorn plantain (*Plantago lanceolata L.*), curly dock (*Rumex crispus L.*), wild mustard (*Brassica kaber DG.*), purslane (*Portulaca oleracea L.*), and barnyard-grass (*Echinochloa crusgalli L.*).

Illustratively, control and significant growth retardation of the foregoing weed species has been achieved using the compounds of this invention at rates of from ¼ to 50 lbs. per acre. Depending upon the kinds of weeds to be controlled, the stage of weed development, the degree of infestation, and the presence or absence of aesthetic or crop plants, the compounds of this invention can be applied to soil, germinating weed seeds, weed seedlings, plant growth media, growing plants, or any other selected situs for control of weeds at rates ranging from about ¼ to 1/2 lb. per acre up to about 50 lbs. per acre. Ordinarily, the situs will be soil, but this term is used in the broad sense — anywhere where weed growth might be a problem, e.g., gravel driveways, railroad beds, flat built-up roofs, ponds, lakes, streams, and canals. Aquatic applications effectively use about 2 to about 10,000 or more, parts per million (ppm), by weight.

The compounds of Formula I can be applied to a situs in a dispersible pure form, but dispersible formulations for herbicidal use are preferred. The dispersible formulations of this invention comprise a compound of the Forumla I in a homogeneous, dispersible form with a homogeneous dispersible carrier. Adjuvants such as surfactants, humectants, dispersants, adhesive or sticking or spreading agents, corrosion inhibitors, and anti-foaming agents can be included.

A homogeneous dispersible carrier comprehends a particulate solid carrier or a liquid carrier diluent. The compound can be dispersed in a liquid carrier diluent as a solute or as finely divided particles (suspension).

The term "dispersible", as used in this specification and in the claims, means matter in a liquid or particulate state such that it can be evenly distributed over a given area or metered into a body of water. A "liquid" state includes true solutions as well as dispersions of particulate solids in a liquid. Emulsions of one liquid in another, e.g., oil-in-water, are also contemplated. The active compound can be in either the dispersed phase, the continuous phase, or partitioned between them both. In general, the active compound will be preponderantly in the dispersed phase when emulsions are used. A "particulate" state includes the general concept of finely divided separate particles, and granular particles as large as 10 mesh (U.S.) or even somewhat larger when appropriate herbicidal practice indicates an advantage in using larger granules.

The granular particles could be included in what is termed an "interstitial" state, which contemplates the deposition or entrapment of the active compound within the interstices of a porous body. For example, the compounds can be mixed with an elastomer, e.g., natural rubber, chloroprene, butyl rubber, polyether and polyester urethanes and the like, which may be further processed according to conventional techniques in the elastomeric art. The latter elastomeric matrices as well as conventional granules provide a slow, sustained release of the active herbicide so that herbicidal concentrations of the active compound can be obtained over a prolonged interval for the control of weeds.

Illustrative of the adjuvants named above, humectants include glycerol, diethylene glycol, solubilized lignins (such as calcium ligninsulfonate), and the like. Dispersants include bentonite, sodium, ammonium, calcium or aluminum ligninsulfonate, condensed naphthalene sulfonate and the like. Adhesive or sticking agents include vegetable oils, naturally occurring gums, casein, and the like. A suitable corrosion inhibitor is epichlorohydrin, and suitable anti-foaming agents such as fatty acids, e.g., sodium stearate; and silicones.

Representative surfactants include alkyl sulfates and sulfonates, alkyl aryl sulfonates, sulfosuccinate esters, polyoxyethylene sulfates, polyoxyethylene-sorbitan esters, e.g., monolaurate, alkyl aryl polyether sulfates, alkyl aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids or alcohols, and the like.

Suitable surfactants include blends of alkyl aryl sulfonates and polyalcohol carboxylic acid esters (Emcol H-77), blends of polyoxyethylene ethers and oil-soluble sulfonates (Emcol H-400), blends of alkyl aryl sulfonates and alkylphenoxy polyethoxy ethanols (Tritons X-151, X-161, and X-171), e.g., about equal parts of sodium aryl or alkylbenzene sulfonate and isooctylphenoxy polyethoxy ethanol containing about 12 ethoxy groups, and blends of calcium alkyl aryl sulfonates and polyethoxylated vegetable oils (Agrimul $N_4S$). It will be understood, or course, that the sulfate and sulfonate surfactants suggested above will preferably be used in the form of their soluble salts, for example, their sodium salts. All of these surfactants are capable of reducing the surface tension of water to less than about 40 dynes per centimeter in concentrations of about 1% or less. The dispersible powder formulations can be prepared with a mixture of surfactants of the types indicated if desired.

The concentration of the active compound of the Formula I according to this invention, in the new herbicidal formulations of this invention is not usually a critical, limiting factor in achieving a desired herbicidal effect. The most important factor is how much compound is applied to an area of weeds to be controlled. It is readily apparent that one can apply a large amount of a formulation having a low concentration of active compound or a relatively small amount of a formulation having a high concentration. Whether a low or high concentration should be used depends upon the mode of application, the amount and kinds of vegetation, and the thoroughness of coverage desired. The total amount to be applied depends upon the kinds of weeds and crop, if any, the severity of infestation, the stage of plant development, and the season of the year.

Representative homogeneous dispersible formulations according to this invention include sprays, dusts, and granular formulations. Spray formulations are preferred for foliar applications and for uniformly controlled applications to a soil. Granular formulations are usually applied in bands spanning the seeded row, although broadcast distribution is advantageous when soil incorporation is practiced and a prolonged effect is desired.

The spray formulations in accordance with the invention can be aqueous solutions, aqueous suspensions, water-in-oil emulsions, oil-in-water emulsions, and oil solutions. The spray formulations will conveniently comprise from about 0.1% or lower to about 50% by weight or even higher, a volume of spray being applied so that a herbicidally effective amount of compound of Formula I is distributed over the treated area. Sprays containing about 0.25 ounce to about 16 lbs. of compound of Formula I in a 20 gal. to 40 gal. volume are applied to foliage or soil for effective herbicidal action.

Concentrates for preparing spray formulations are advantageously prepared by dissolving the active compounds of the invention in a solvent, or by dispersing the active compounds in a dispersible solid or liquid carrier diluent. Illustratively, the herbicidally active compound of Formula I of this invention is dissolved or dispersed in water or a suitable water-miscible or water-immiscible inert organic liquid. Representative water-miscible organic liquids include acetone, methyl ethyl ketone, dimethylformamide, alcohols, monoalkyl ethers of ethylene glycol, ethyl acetate, and the like. Representative substantially water-immiscible organic liquids (i.e., a solvent carrier which is soluble in water to the extent of less than 2.5% by volume at temperatures of the order of 20° to 30° C.) for preparing emulsifiable concentrates include petroleum oils, distillates, toluene, xylene, cumene, and like aromatic hydrocarbons, isoparaffin oil, mineral oil, and the like.

Advantageously, the concentration of active ingredient in the emulsifiable concentrates (with or without surfactant) can range from about 5 to about 90% by weight, preferably from about 10 to about 40%. A concentrate comprising 20% (by weight) of the compound dissolved in a water-immiscible solvent of the kind noted above can be admixed with an aqueous medium in the proportions of 13 ml. of concentrate with 1 gal. of medium to give a mixture containing 700 parts of active ingredient per million parts of liquid carrier. Similarly, 1 qt. of a 20% concentrate mixed with 40 gals. of water provides about 1200 ppm (parts per million) of active ingredient. In the same manner, more concentrated solutions of active ingredient can be prepared.

Dust formulations in accordance with the invention are readily prepared by dispersing the active compound in a dispersible solid by grinding a mixture of the compound and a pulverulent solid carrier in the presence of each other. Grinding is conveniently accomplished in a ball mill, a hammermill, or by air-blast micronization. These dust compositions can also be prepared by dissolving the compound of Formula I in a volatile solvent such as methylene chloride, mixing the solution with a pulverulent solid carrier, evaporating the solvent, and pulverizing the impregnated carrier. A suitable ultimate particle size is less than 60 microns. Preferably, 95% Of the particles are less than 50 microns, and about 75% are 5 to 20 microns. Dusts of this degree of comminution are conveniently free-flowing.

Representative suitable pulverulent solid carriers include the natural clays such as China, Georgia, Barden, Attapulgus, kaolin, and Montmovillonite clays; minerals in their natural forms as they are obtained from the earth such as talc, pyrophyllite, quartz, diatomaceous earth, fuller's earth, chalk, rock phosphates and sulfates, calcium carbonates, sulfur, silica and silicates; chemically modified minerals such as washed bentonite, precipitated calcium phosphate, precipitated calcium carbonate, precipitated calcium silicate, synthetic magnesium silicate, and colloidal silica; and organic flours such as wood, walnut shell, soybean, cottonseed, and tobacco flours, and free-flowing, hydrophobic starches.

The proportions of pulverulent carrier and compound of Formula I can vary over a wide range depending upon the plants to be controlled, rates of application according to equipment available, and the conditions of treatment. In general, dust formulations can contain up to about 90% (on a weight basis) of the active ingredient. Dusts having as little as 0.001% of the active ingredient can be used, but a generally preferred proportion is from about 0.50% to about 20% of active ingredient.

Advantageously, a dust formulation as described above includes a surfactant, because about 0.1% to about 12% of a surfactant promotes dispersibility of a dust in water and facilitates formulation of aqueous sprays or dispersibility of a dust formulation applied directly to water surfaces or aquatic weeds. Dust formulations comprising a surfactant are known as dispersible or wettable powders. As indicated, dispersible or wettable powders can be admixed with water to obtain any desired concentration up to about 50% w/v of active ingredient. The dispersible or wettable powders can conveniently comprise from about 10% to about 90% active ingredient, preferably about 30% to about 80%.

A suitable dispersible powder formulation is obtained by blending and milling 327 lbs. of Georgia Clay, 4.5 lbs. of calcium alkyl aryl benzene sulfonate (NeCal BA77) as a wetting agent, 9 lbs. of a polymerized sodium salt of substituted benzoid long-chain sulfonic acid (Daxad 27) as a dispersing agent, and 113 lbs. of the active ingredient. The resulting formulation has the following percentage composition (parts herein are by weight unless otherwise specified):

| | |
|---|---|
| Active ingredient | 25% |
| Calcium alkyl aryl benzene sulfonate | 1% |
| Polymerized sodium salt of substituted benzoid long-chain sulfonic acid | 2% |
| Georgia Clay | 72% |

This formulation, when dispersed in water at the rate of 10 lbs. per 100 gals., gives a spray formulation containing about 0.3% (3000 ppm) active ingredient which can be applied to weeds at the rate of 40 gals. per acre to give a total application of active ingredient of 1 lb. per acre.

Further in accordance with this invention, formulations of the compounds of the Formula I with oil are particularly efficacious, and herbicidal action of the compound is improved. Any petroleum oil can be used so long as it is not so viscous as to be too difficult to disperse. A nonphytotoxic oil is satisfactory.

Advantageously, a 50% wettable powder of the herbicidal active ingredient is mixed with about 38 gals. water and 2 gals. oil for spray application.

The following examples are illustrative of the process and products of the present invention but are not to be construed as limiting.

EXAMPLE 1

Preparation of
3,4-Dibromo-N,N-$\alpha$,5-tetramethylpyrazole-1-acetamide

Part A - Ethyl
3,4-dibromo-$\alpha$,5-dimethylpyrazole-1-acetate

A reaction mixture consisting of a solution of 13.7 g. (0.057 mole) 4,5-dibromo-3-methylpyrazole in 200 ml. acetone and 15.7 g. (0.114 mole) anhydrous potassium carbonate was heated at the reflux temperature with continuous stirring for 15 minutes. After cooling, 10.4 g. (0.06 mole) ethyl 2-bromopropionate was added. This reaction mixture was then heated at the reflux temperature for 2.5 hours. It was cooled and filtered. The acetone was then removed by evaporation under reduced pressure, and the residue thus obtained was dissolved in hot hexane. After chilling in a refrigerator the crystals that had formed were collected on a filter. There was thus obtained 14.5 g. (75% yield) of ethyl 3,4-dibromo-$\alpha$,5-dimethylpyrazole-1-acetate having a melting point at 61° to 62° C.

Analysis: Calc'd. for $C_9H_{12}Br_2N_2O_2$: C, 31.79; H, 3.56; N, 8.24. Found: C, 31.86; H, 3.55; N, 8.48.

Part B - 3,4-Dibromo-$\alpha$,5-dimethylpyrazole-1-acetic acid

A quantity (5.1 g., 0.015 mole) of the ethyl 3,4-dibromo-$\alpha$,5-dimethylpyrazole-1-acetate prepared in Part A, above, was added to a solution consisting of 0.8 g. (0.02 mole) sodium hydroxide in 100 ml. water and the resulting suspension was heated at the reflux temperature for 3 hrs. A clear, aqueous solution resulted. The aqueous solution was extracted with 50 ml. diethyl ether and the ether extract was discarded. The ether-extracted aqueous layer was then adjusted to pH 2 with 1.5 N hydrochloric acid and again extracted three times with 40 ml. portions of the ether. These ether extracts were combined, washed with three, 30 ml. portions of water, dried over anhydrous magnesium sulfate, and the ether was removed by evaporation under reduced pressure. There was thus obtained 4.0 g. (85% yield) of 3,4-dibromo-$\alpha$,5-dimethylpyrazole-1-acetic acid having a melting point at 131° to 135.5° C. Recrystallization from a mixture of acetone and hexane gave the compound with a melting point at 138° C.

Analysis: Calc'd. for $C_7H_8Br_2N_2O_2$: C, 26.95; H, 2.59; N, 8.98. Found: C, 27.07; H, 2.61; N, 9.10.

Part C - The desired 3,4-Dibromo-N,N,$\alpha$,5-tetramethylpyrazole-1-acetamide

A suspension consisting of 1.7 g. (0.0055 mole) of the 3,4-dibromo-$\alpha$,5-dimethylpyrazole-1-acetic acid prepared in Part B, above, in 10 ml. thionyl chloride was heated at the reflux temperature for 2.5 hours. The excess thionyl chloride was then removed by evaporation under reduced pressure to give the expected 3,4-dibromo-$\alpha$,5-dimethylpyrazole-1-acetyl chloride which was dissolved in 100 ml. benzene. This benzene solution was added dropwise with stirring to a solution consisting of 2 ml. dimethylamine and 25 ml. benzene. After the addition of the acid chloride had been completed, the reaction mixture was stirred continuously for 1 hour while the temperature was 25° C. It was then heated at the reflux temperature for another hour. After cooling, the reaction solution was washed three times with 30 ml. portions of water and then dried over anhydrous magnesium sulfate. The washed and dried benzene solution was concentrated by evaporation under reduced pressure. An oil was obtained that was very slow to crystallize. Recrystallization from a mixture consisting of methylene chloride and Skellysolve F (a petroleum ether fraction with a boiling point between 30°–60° C.) gave 3,4-dibromo-N,N,$\alpha$,5-tetramethylpyrazole-1-acetamide having a melting point at 56° to 58.5° C. [About 10% of the 4,5-dibromo-N,N,$\alpha$,3-tetramethylpyrazole-1-acetamide isomer was present].

Analysis: Calc'd. for $C_9H_{13}Br_2N_3O$: C, 31.88; H, 3.86; N, 12.40. Found: C, 32.20; H, 3.88; N, 12.80.

The separation and identification of the isomers is described in Example 35.

EXAMPLE 2

3,4-Dibromo-N-ethyl-N,$\alpha$,5-trimethylpyrazole-1-acetamide

Following the procedure of Example 1, Part C, but substituting ethylmethylamine for dimethylamine, there was prepared the corresponding 3,4-dibromo-N-ethyl-N,$\alpha$,5-trimethylpyrazole-1-acetamide having a melting point at 55° to 56.5° C.

Analysis: Calc'd. for $C_{10}H_{15}Br_2N_3O$: C, 34.02; H, 4.28; N, 11.90. Found: C, 33.80; H, 4.21; N, 11.66.

EXAMPLE 3

3,4-Dibromo-N-isopropyl-N,$\alpha$,5-trimethylpyrazole-1-acetamide

Following the procedure of Example 1, Part C, but substituting isopropylmethylamine for dimethylamine, there was prepared the corresponding 3,4-dibromo-N-isopropyl-N,$\alpha$,5-trimethylpyrazole-1-acetamide having a melting point of 95° to 96.5° C.

Analysis: Calc'd. for $C_{11}H_{17}Br_2N_3O$: C, 35.99; H, 4.67; N, 11.45. Found: C, 35.92; H, 4.69; N, 11.10.

EXAMPLE 4

3,4-Dibromo-N-benzyl-N,$\alpha$,5-trimethylpyrazole-1-acetamide

Following the procedure of Example 1, Part C, but substituting benzylmethylamine, for dimethylamine, there was prepared the corresponding 3,4-dibromo-N-benzyl-N,$\alpha$,5-trimethylpyrazole-1-acetamide having a melting point at 58° to 59° C.

Analysis: Calc'd. for $C_{15}H_{17}Br_2N_3O$: C, 43.39; H, 4.13; N, 10.12. Found: C, 43.12; H, 4.00; N, 10.23.

EXAMPLE 5

3,4-Dibromo-N,N-diethyl-$\alpha$,5-dimethylpyrazole-1-acetamide

Following the procedure of Example 1, Part C, but substituting diethylamine for dimethylamine, there was prepared the corresponding 3,4-dibromo-N,N-diethyl-$\alpha$,5-dimethylpyrazole-1-acetamide having a melting point at 49° to 50° C.

Analysis: Calc'd. for $C_{11}H_{17}Br_2N_3O$: C, 35.99; H, 4.67; N, 11.44; Br, 43.54. Found: C, 35.84; H, 4.63; N, 11.60; Br, 43.81.

EXAMPLE 6

3,4-Dibromo-N-ethyl-N-isopropyl-$\alpha$,5-dimethylpyrazole-1-acetamide

Following the procedure of Example 1, Part C, but substituting ethylisopropylamine for dimethylamine, there was prepared the corresponding 3,4-dibromo-N-ethyl-N-isopropyl-$\alpha$,5-dimethylpyrazole-1-acetamide having a melting point at 81° to 81.5° C.

Analysis: Calc'd. for $C_{12}H_{19}Br_2N_3O$: C, 37.81; H, 5.02; N, 11.03; Br, 41.94. Found: C, 37.91; H, 4.96; N, 11.06; Br, 41.95.

EXAMPLE 7

3,4-Dibromo-N,N-di-n-propyl-$\alpha$,5-dimethylpyrazole-1-acetamide

Following the procedure of Example 1, Part C, but substituting di-n-propylamine for dimethylamine, there was prepared the corresponding 3,4-dibromo-N,N-di-n-propyl-$\alpha$,5-dimethylpyrazole-1-acetamide having a melting point at 92° to 94° C.

Analysis: Calc'd. for $C_{13}H_{21}Br_2N_3O$: C, 39.51; H, 5.36; N, 10.63; Br, 40.45. Found: C, 39.49; H, 5.25; N, 10.53; Br, 40.43.

EXAMPLE 8

3,4-Dibromo-N,N-diallyl-$\alpha$,5-dimethylpyrazole-1-acetamide

Following the procedure of Example 1, Part C, but substituting diallylamine for dimethylamine, there was prepared the corresponding 3,4-dibromo-N,N-diallyl-$\alpha$,5-dimethylpyrazole-1-acetamide having a melting point at 81° to 82° C.

Analysis: Calc'd. for $C_{13}H_{17}Br_2N_3O$: C, 39.92; H, 4.38; N, 10.74. Found: C, 39.71; H, 4.23; N, 10.86.

EXAMPLE 9

1-[2-(3,4-Dibromo-5-methylpyrazole-1-yl)propionyl]-pyrrolidine

Following the procedure of Example 1, Part C, but substituting pyrrolidine for dimethylamine, there was prepared the corresponding 1-[2-(3,4-dibromo-5-methylpyrazole-1-yl)propionyl]pyrrolidine having a melting point at 94° to 95.5° C.

Analysis: Calc'd. for $C_{11}H_{15}Br_2N_3O$: C, 36.19; H, 4.14; N, 11.51. Found: C, 36.28; H, 4.15; N, 11.35.

EXAMPLE 10

4-[2-(3,4-Dibromo-5-methylpyrazol-1-yl)propionyl]-morpholine

Following the procedure of Example 1, Part C, but substituting morpholine for dimethylamine, there was prepared the corresponding 4-[2-(3,4-dibromo-5-methylpyrazol-1-yl)propionyl]morpholine having a melting point at 128° to 130° C.

Analysis: Calc'd. for $C_{11}H_{15}Br_2N_3O_2$: C, 34.67; H, 3.97; N, 11.03; Br, 41.94. Found: C, 34.58; H, 3.78; N, 11.34; Br, 41.98.

EXAMPLE 11

3,4-Dibromo-α,5-dimethyl-N,N-diphenylpyrazole-1-acetamide

Following the procedure of Example 1, Part C, but substituting diphenylamine for dimethylamine there was prepared the corresponding 3,4-dibromo-α,5-dimethyl-N,N-diphenylpyrazole-1-acetamide having a melting point at 162° to 163° C.

Analysis: Calc'd. for $C_{19}H_{17}Br_2N_3O$: C, 49.27; H, 3.70; N, 9.07; Br, 34.51. Found: C, 49.12; H, 3.65; N, 8.98; Br, 34.66.

EXAMPLE 12

3,4-Dibromo-N,α,5-trimethylpyrazole-1-acetamide

Following the procedure of Example 1, Part C, but substituting methylamine for dimethylamine, there was prepared the corresponding 3,4-dibromo-N,α,5-trimethylpyrazole-1-acetamide having a melting point at 195° to 197° C.

Analysis: Calc'd. for $C_8H_{11}Br_2N_3O$: C, 29.56; H, 3.41; N, 12.95. Found: C, 29.75; H, 3.41; N, 13.35.

EXAMPLE 13

3,4-Dibromo-N-allyl-α,5-dimethylpyrazole-1-acetamide

Following the procedure of Example 1, Part C, but substituting allylamine for dimethylamine, there was prepared the corresponding 3,4-dibromo-N-allyl-α,5-dimethylpyrazole-1-acetamide having a melting point at 168° to 169° C.

Analysis: Calc'd. for $C_{10}H_{13}Br_2N_3O$: C, 34.21; H, 3.73; N, 11.97. Found: C, 33.94; H, 3.73; N, 11.78.

EXAMPLE 14

3,4-Dibromo-N-cyclohexyl-α,5-dimethylpyrazole-1-acetamide

Following the procedure of Example 1, Part C, but substituting cyclohexylamine for dimethylamine, there was prepared the corresponding 3,4-dibromo-N-cyclohexyl-α,5-dimethylpyrazole-1-acetamide having a melting point at 208° to 209° C.

Analysis: Calc'd. for $C_{13}H_{19}Br_2N_3O$: C, 39.71; H, 4.87; N, 10.69. Found: C, 39.51; H, 4.85; N, 10.43.

EXAMPLE 15

3,4-Dibromo-α,5-dimethylpyrazole-1-acetanilide

Following the procedure of Example 1, Part C, but substituting aniline for dimethylamine, there was prepared the corresponding 3,4-dibromo-α,5-dimethylpyrazole-1-acetanilide having a melting point at 184.5° to 185° C.

Analysis: Calc'd. for $C_{13}H_{13}Br_2N_3O$: C, 40.34; H, 3.38; N, 10.86; Br, 41.30. Found: C, 40.60; H, 3.28; N, 10.54; Br, 41.19.

EXAMPLE 16

3,4-Dibromo-3',4'-dichloro-α,5-dimethylpyrazole-1-acetanilide

Following the procedure of Example 1, Part C, but substituting 3,4-dichloroaniline for dimethylamine, there was prepared the corresponding 3,4-dibromo-3',4'-dichloro-α,5-dimethylpyrazole-1-acetanilide having a melting point at 182.5° to 184° C.

Analysis: Calc'd. for $C_{13}H_{11}Br_2Cl_2N_3O$: C, 34.24; H, 2.43; N, 9.22. Found: C, 34.11; H, 2.43; N, 9.25.

EXAMPLE 17

Preparation of 3,4-Dibromo-N,N,5-trimethylpyrazole-1-acetamide

Part A - Ethyl 3,4-dibromo-5-methylpyrazole-1-acetate

Following the procedure of Example 1, Part A, but substituting ethyl bromoacetate for ethyl 2-bromopropionate, there was prepared ethyl 3,4-dibromo-5-methylpyrazole-1-acetate having a melting point at 98° to 100° C.

Analysis: Calc'd. for $C_8H_{10}Br_2N_2O_2$: C, 29.47; H, 3.09; N, 8.59. Found: C, 29.66; H, 3.02; N, 8.45.

Part B - 3,4-Dibromo-5-methylpyrazole-1-acetic acid

Following the procedure of Example 1, Part B, but substituting the ethyl 3,4-dibromo-5-methylpyrazole-1-acetate prepared in Part A, above, for the ethyl 3,4-dibromo-α,5-dimethylpyrazole-1-acetate, there was prepared 3,4-dibromo-5-methylpyrazole-1-acetic acid having a melting point at 221° to 222.5° C.

Analysis: Calc'd. for $C_6H_6Br_2N_2O_2$: C, 24.18; H, 2.03; N, 9.40. Found: C, 24.43; H, 2.07; N, 9.33.

Part C - 3,4-Dibromo-N,N,5-trimethylpyrazole-1-acetamide

Following the procedure of Example 1, Part C, but substituting the 3,4-dibromo-5-methylpyrazole-1-acetic acid prepared in Part B, above, for the 3,4-dibromo-α,5-dimethylpyrazole-1-acetic acid, there was prepared 3,4-dibromo-N,N,5-trimethylpyrazole-1-acetamide having a melting point at 106.5° to 108° C.

Analysis: Calc'd. for $C_8H_{11}Br_2N_3O$:
C, 29.56; H, 3.41; N, 12.93. Found: C, 29.53; H, 3.43; N, 12.59.

EXAMPLE 18

3,4-Dibromo-N,5-dimethylpyrazole-1-acetamide

Following the procedure of Example 1, Part C, but substituting methylamine for the dimethylamine, and further substituting the 3,4-dibromo,5-methylpyrazole-1-acetic acid prepared in Example 17, Part B, above, for the 3,4-dibromo-α,5-dimethylpyrazole-1-acetic acid, there was prepared the corresponding 3,4-dibromo-N,5-dimethylpyrazole-1-acetamide having a melting point at 181° to 181.5° C.

Analysis: Calc'd. for $C_7H_9Br_2N_3O$: C, 27.03; H, 2.92; N, 13.51. Found: C, 27.04; H, 2.92; N, 13.21.

EXAMPLE 19

3,4-Dibromo-N-ethyl-N,5-dimethylpyrazole-1-acetamide

Following the procedure of Example 1, Part C, but substituting ethylmethylamine for the dimethylamine, and further substituting the 3,4-dibromo-5-methylpyrazole-1-acetic acid prepared in Example 17, Part B, above, for the 3,4-dibromo-α,5-dimethylpyrazole-1-acetic acid, there was prepared the corresponding 3,4-dibromo-N-ethyl-N,5-dimethylpyrazole-1-acetamide having a melting point at 94° to 95° C.

Analysis: Calc'd. for $C_9H_{13}Br_2N_3O$: C, 31.88; H, 3.86; N, 12.39. Found: C, 31.82; H, 3.80; N, 12.35.

EXAMPLE 20

3,4-Dibromo-N,N-diethyl-5-methylpyrazole-1-acetamide

Following the procedure of Example 1, Part C, but substituting diethylamine for the dimethylamine, and further substituting the 3,4-dibromo-5-methylpyrazole-1-acetic acid prepared in Example 17, Part B, above, for the 3,4-dibromo-α,5-dimethylpyrazole-1-acetic acid, there was prepared the corresponding 3,4-dibromo-N,N-diethyl-5-methylpyrazole-1-acetamide having a melting point at 83° to 85° C.

Analysis: Calc'd. for $C_{10}H_{15}Br_2N_3O$: C, 34.02; H, 4.28; N, 11.90. Found: C, 33.90; H, 4.23; N, 11.78.

EXAMPLE 21

3,4-Dibromo-5-methyl-N,N-di-n-propylpyrazole-1-acetamide

Following the procedure of Example 1, Part C, but substituting di-n-propylamine for the dimethylamine, and further substituting the 3,4-dibromo-5-methylpyrazole-1-acetic acid prepared in Example 17, Part B, above, for the 3,4-dibromo-α,5-dimethylpyrazole-1-acetic acid, there was prepared the corresponding 3,4-dibromo-5-methyl-N,N-di-n-propylpyrazole-1-acetamide having a melting point at 58° to 60° C.

Analysis: Calc'd. for $C_{12}H_{19}Br_2N_3O$: C, 37.81; H, 5.02; N, 11.03. Found: C, 37.51; H, 4.99; N, 11.14.

EXAMPLE 22

Preparation of 3,4-Dibromo-α-ethyl-N,N,5-trimethylpyrazole-1-acetamide

Part A - Ethyl 3,4-dibromo-α-ethyl-5-methylpyrazole-1-acetate

Following the procedure of Example 1, Part A, but substituting ethyl 2-bromobutyrate for ethyl 2-bromopropionate there was prepared ethyl 3,4-dibromo-α-ethyl-5-methylpyrazole-1-acetate having a boiling point at 147° C. and 0.07 mm Hg. pressure.

Analysis: Calc'd. for $C_{10}H_{14}Br_2N_2O_2$: C, 33.92; H, 3.99; N, 7.91. Found: C, 33.72; H, 3.90; N, 7.82.

Part B - 3,4-Dibromo-α-ethyl-5-methylpyrazole-1-acetic acid

Following the procedure of Example 1, Part B, but substituting the ethyl 3,4-dibromo-α-ethyl-5-methylpyrazole-1-acetate prepared in Part A, above, for the ethyl 3,4-dibromo-α,5-dimethylpyrazole-1-acetate, there was prepared 3,4-dibromo-α-ethyl-5-methylpyrazole-1-acetic acid having a melting point at 98° to 101° C.

Analysis: Calc'd. for $C_8H_{10}Br_2N_2O_2$: C, 29.47; H, 3.09; N, 8.59. Found: C, 29.58; H, 3.15; N, 8.61.

Part C - 3,4-Dibromo-α-ethyl-N,N,5-trimethylpyrazole-1-acetamide

Following the procedure of Example 1, Part C, but substituting the 3,4-dibromo-α-ethyl-5-methylpyrazole-1-acetic acid prepared in Part B, above, for the 3,4-dibromo-α,5-dimethylpyrazole-1-acetic acid, there was prepared 3,4-dibromo-α-ethyl-N,N,5-trimethylpyrazole-1-acetamide having a melting point at 74° to 75.5° C.

Analysis: Calc'd. for $C_{10}H_{15}Br_2N_3O$: C, 34.02; H, 4.28; N, 11.90. Found: C, 34.21; H, 4.19; N, 11.89.

EXAMPLE 23

3,4-Dibromo-α,N-diethyl-N,5-dimethylpyrazole-1-acetamide

Following the procedure of Example 1, Part C, but substituting ethylmethylamine for dimethylamine and further substituting the 3,4-dibromo-α-ethyl-5-methylpyrazole-1-acetic acid prepared in Example 22, Part B, above, for the 3,4-dibromo-α,5-dimethylpyrazole-1-acetic acid, there was prepared the corresponding 3,4-dibromo-α,N-diethyl-N,5-dimethylpyrazole-1-acetamide having a melting point at 58.5° to 61° C.

Analysis: Calc'd. for $C_{11}H_{17}Br_2N_3O$: C, 35.99; H, 4.67; N, 11.45. Found: C, 36.06; H, 4.76; N, 11.46.

EXAMPLE 24

3,4-Dibromo-N,N,α-triethyl-5-methylpyrazole-1-acetamide

Following the procedure of Example 1, Part C, but substituting diethylamine for dimethylamine and further substituting the 3,4-dibromo-α-ethyl-5-methylpyrazole-1-acetic acid prepared in Example 22, Part B, above, for the 3,4-dibromo-α,5-dimethylpyrazole-1-acetic acid, there was prepared the corresponding 3,4-dibromo-N,N,α-triethyl-5-methylpyrazole-1-acetamide having a melting point at 70° to 70.5° C.

Analysis: Calc'd. for $C_{12}H_{19}Br_2N_3O$: C, 37.81; H, 5.02; N, 11.03. Found: C, 37.96; H, 4.93; N, 10.91.

EXAMPLE 25

Preparation of 3,4-Dibromo-N,N,5-trimethyl-α-phenylpyrazole-1-acetamide

Part A - Ethyl 3,4-dibromo-5-methyl-α-phenylpyrazole-1-acetate

Following the procedure of Example 1, Part A, but substituting ethyl 2-bromophenyl acetate for ethyl-2-bromopropionate, there is prepared ethyl 3,4-dibromo-5-methyl-α-phenylpyrazole-1-acetate as a brown oil which was not further purified.

Part B - 3,4-Dibromo-5-methyl-α-phenylpyrazole-1-acetic acid

Following the procedure of Example 1, Part B, but substituting the ethyl 3,4-dibromo-5-methyl-α-phenylpyrazole-1-acetate prepared in Part A, above, for ethyl 3,4-dibromo-α,5-dimethylpyrazole-1-acetate, there was prepared 3,4-dibromo-5-methyl-α-phenylpyrazole-1-acetic acid having a melting point at 130° to 131° C.

Analysis: Calc'd. for $C_{12}H_{10}Br_2N_2O_2$: C, 38.53; H, 2.69; N, 7.49. Found: C, 38.74; H, 2.77; N, 7.59.

Part C -
3,4-Dibromo-N,N,5-trimethyl-α-phenylpyrazole-1-acetamide

Following the procedure of Example 1, Part C, but substituting the 3,4-dibromo-5-methyl-α-phenylpyrazole-1-acetic acid prepared in Part B, above, for the 3,4-dibromo-α,5-dimethylpyrazole-1-acetic acid, there was prepared 3,4-dibromo-N,N,5-trimethyl-α-phenylpyrazole-1-acetamide having a melting point at 195° to 196° C.

Analysis: Calc'd. for $C_{14}H_{15}Br_2N_3O$: C, 41.92; H, 3.77; N, 10.48; Br, 39.85. Found: C, 42.03; H, 3.87; N, 10.58; Br, 39.64.

EXAMPLE 26

Preparation of
3,4-Dibromo-N,N,α,α,5-pentamethylpyrazole-1-acetamide

Part A - 3,4-Dibromo-α,α,5-trimethylpyrazole-1-acetic acid Sodium hydride (2.2 g., 0.055 mole) (60% oily dispersion) was stirred for 3 minutes with dry toluene (100 ml.) and then the toluene removed. A further 30 ml. of dry toluene was added, followed by a solution of 4,5-dibromo-3-methylpyrazole (12.05 g., 0.05 mole) in toluene (60 ml.). The mixture was heated under reflux and ethyl 2-bromoisobutyrate (10.73 g., 0.055 mole) was added drop by drop. The reaction mixture was heated at reflux for 48 hours, cooled, and treated with water (50 ml.), the organic layer separated and evaporated under reduced pressure. To the resultant orange oil, a solution of sodium hydroxide (2.4 g., 0.06 mole) in water (100 ml.) was added and heated under reflux for 6 hours. The solution was cooled, extracted with ether (2 × 70 ml.), the ether layer discarded and the aqueous layer acidified to pH 4 with 3 N hydrochloric acid. The resultant oil was extracted with ether (2 × 90 ml.), the ether layer washed with water, dried, and the solvent removed under reduced pressure to yield 3,4-dibromo-α,α,5-trimethylpyrazole-1-acetic acid, having a melting point at 160° to 161° C.

Analysis: Calc'd. for $C_8H_{10}Br_2N_2O_2$: C, 29.47; H, 3.09; N, 8.59; Br, 49.03. Found: C, 29.64; H, 3.17; N, 8.36; Br, 49.05.

Part B -
3,4-Dibromo-N,N,α,α,5-pentamethylpyrazole-1-acetamide

A solution of the above prepared 3,4-dibromo-α,α,5-trimethylpyrazole-1-acetic acid (3.91 g., 0.012 mole) in benzene (10 ml.) and thionyl chloride (4.72 g., 0.04 mole) was heated under reflux for 4 hours, cooled and evaporated under reduced pressure. The resultant oil was dissolved in benzene (20 ml) and added dropwise to a stirred solution of excess dimethylamine (25 ml.) in benzene (20 ml.) and the mixture heated under reflux for 30 minutes. The benzene layer was washed with water and then evaporated under reduced pressure to yield a solid (3.7 g.) which on recrystallization from hexane yielded 3,4-dibromo-N,N,α,α,5-pentamethylpyrazole-1-acetamide having a melting point at 111° to 113° C.

Analysis: Calc'd. for $C_{10}H_{15}Br_2N_3O$: C, 34.02; H, 4.28; N, 11.90. Found: C, 34.07; H, 4.28; N, 11.96.

EXAMPLE 27

Preparation of
3,5-Dibromo-N,N,α,4-tetramethylpyrazole-1-acetamide

Part A - 3,5-Dibromo-4-methylpyrazole

With continuous stirring, a 1.6 M solution of butyl lithium in 260 ml. hexane (0.4 mole) was added during an interval of 60 minutes to a solution consisting of 30.4 g. (0.1 mole) tribromopyrazole and 130 ml. diethyl ether in an environment of pure gaseous nitrogen at minus 30° C. After this addition, the stirring was continued for a further interval of 3 hours after which interval the temperature of the mixture was lowered to minus 70° C. (−70° C.) and 56.8 g. (0.4 mole) methyl iodide was added. This mixture was allowed to warm to about 25° C. Again with vigorous stirring, 100 ml. water was added while maintaining the temperature below 25° C. A two-phased body of liquid resulted and the organic phase was separated and discarded. The retained aqueous phase was made acid with 3 N hydrochloric acid and a white precipitate formed. The precipitate was collected on a filter, the filter cake was dissolved in hot hexane, and the hexane solution was chilled in a refrigerator. Crystals formed and there was obtained 5.5 g. of 3,5-dibromo-4-methylpyrazole having a melting point at 156° to 158° C.

Analysis: Calc'd. for $C_4H_4Br_2N_2$: C, 20.02; H, 1.68; N, 11.68; Br, 66.62 Found: C, 19.87; H, 1.68; N, 11.90; Br, 66.68.

Part B -
3,5-Dibromo-N,Nα,4-tetramethylpyrazole-1-acetamide

A small quantity (0.48 g., 0.002 mole) of the 3,5-dibromo-4-methylpyrazole prepared in Part A, above, was dissolved in aqueous sodium hydroxide prepared by mixing 2 ml. of 2 N sodium hydroxide and 3 ml. water, and 0.3 g. (0.0022 mole) N,N-dimethyl-2-chloropropionamide was added. The reaction mixture was heated at the reflux temperature for 50 minutes while the pH was kept adjusted to pH 9. The refluxed mixture was then cooled, diluted with 10 ml. water, and extracted with three-10 ml. portions of diethyl ether. The ether extracts were combined, washed with 10 ml. water, and dried over anhydrous magnesium sulfate. After removing the ether by evaporation under reduced pressure, there was obtained a white powder weighing 0.42 g. that after crystallization from hexane was identifiable as the desired 3,5-dibromo-N,N,α,4-tetramethylpyrazole-1-acetamide having a melting point at 111° to 112° C.

Analysis: Calc'd. for $C_9H_{13}Br_2N_3O$: C, 31.88; H, 3.86; N, 12.40. Found: C, 32.07; H, 3.90; N, 12.18.

EXAMPLE 28

3,5-Dibromo-N,N-diethyl-α,4-dimethylpyrazole-1-acetamide

Sodium hydride (1.6 g., 0.04 mole) (60% oily dispersion) was stirred with dry toluene (20 ml.) for 5 minutes and then the toluene removed. A further 40 ml. of dry toluene was added, followed by a solution of 3,5-dibromo-4-methylpyrazole (4.8 g., 0.02 mole) in toluene (40 ml.). The mixture was heated under reflux and 2-chloro-N,N-diethylpropionamide (6.55 g., 0.04 mole) was added drop by drop. The reaction mixture was heated at reflux for a further 45 minutes, cooled and treated with toluene (30 ml.) and water (70 ml.). The toluene layer was washed with water (2 × 70 ml.), dried over magnesium sulfate, filtered and the solvent removed under reduced pressure. The solid residue was crystallized from hexane to yield 3,5-dibromo-N,N-diethyl-α,4-dimethylpyrazole-1-acetamde. having a melting point at 75° to 77° C.

Analysis: Calc'd. for $C_{11}H_{17}Br_2N_3O$: C, 35.99; H, 4.67; N, 11.45; Br, 43.54. Found: C, 36.15; H, 4.76; N, 11.37; Br, 43.78.

EXAMPLE 29

3,5-Dibromo-N,N-diethyl-4-methylpyrazole-1-acetamide

Following the procedure of Example 26, but substituting 2-chloro-N,N-diethylacetamide for 2-chloro-N,N-diethylpropionamide there was prepared the corresponding 3,5-dibromo-N,N-diethyl-4-methylpyrazole-1-acetamide, having a melting point at 98° to 99° C.

Analysis: Calc'd. for $C_{10}H_{15}Br_2N_3O$: C, 34.02; H, 4.28; N, 11.90; Br, 45.27.
Found: C, 34.01; H, 4.29; N, 11.90; Br, 45.36.

EXAMPLE 30

Preparation of 3,4-dibromo-5-ethyl-N,N,α-trimethylpyrazole-1-acetamide and 4,5-dibromo-3-ethyl-N,N,α-trimethylpyrazole-1-acetamide

Part A - 4,5-Dibromo-3-ethylpyrazole

To a stirred suspension of sodium acetate (10.16 g., 0.124 mole) in acetic acid (30 ml.) and water (5 ml.), 3-ethylpyrazole (4.8 g., 0.05 mole) was added, followed by dropwise addition of bromine (19.2 g., 0.12 mole) keeping the internal temperature below 35° C. The mixture was kept at room temperature for 48 hours, treated with water (150 ml.) containing sodium bisulfite (2.5 g.) and filtered. Recrystallization of the white precipitate from hexane gave 4,5-dibromo-3-ethylpyrazole (9.9 g., 78%) with a melting point at 99° to 100° C.

Analysis: Calc'd. for $C_5H_6Br_2N_2$: C, 23.64; H, 2.38; N, 11.03; Br, 62.94. Found: C, 23.83; H, 2.44; N, 11.37; Br, 62.99.

Part B - 3,4-Dibromo-5-ethyl-N,N,α-trimethylpyrazole-1-acetamide and 4,5-dibromo-3-ethyl-N,N,α-trimethylpyrazole-1-acetamide Sodium hydride (0.757 g., 0.018 mole) (57% oily dispersion) was washed with dry toluene (2 × 30 ml.) and then suspended in dry toluene (30 ml.). A solution of 4,5-dibromo-3-ethylpyrazole (3.81 g., 0.015 mole) in toluene (75 ml.) was added to the sodium hydride suspension, the mixture heated under reflux for 10 minutes and then treated with a solution of 2-chloro-N,N-dimethylpropionamide (2.43 g., 0.018 mole) in toluene (6 ml.) drop by drop during 5 minutes. Heating was continued for two hours, the mixture cooled and treated with toluene (60 ml.) and water (40 ml.). The toluene layer was washed with water (2 × 40 ml.), dried over magnesium sulfate, and the solvent removed under reduced pressure. The resulting solid (95% yield) was chromatographed on a silica gel column using ether-chloroform or benzene-ethyl acetate as solvent systems. The first compound eluted from the column was identified as 4,5-dibromo-3-ethyl-N,N,α-trimethylpyrazole-1-acetamide (60%) with a melting point at 61° to 63° C. and a retention time of 5.5 minutes in a gas-liquid chromatography system employing a QFI column at 175° C.

Analysis: Calc'd. for $C_{10}H_{15}Br_2N_3O$: C, 34.01; H, 4.29; N, 11.90; Br, 45.26. Found: C, 34.11; H, 4.19; N, 12.14; Br, 45.22.

Further elution of the column yielded a second compound that was identified as 3,4-dibromo-5-ethyl-N,N,α-trimethylpyrazole-1-acetamide (40%) with a melting point at 94° to 95° C., and a retention time of 10.5 minutes in a gas-liquid chromatography system employing a QFI column at 175° C.

Analysis: Calc'd. for $C_{10}H_{15}Br_2N_3O$: C, 34.01; H, 4.29; N, 11.90; Br, 45.26. Found: C, 34.01; H, 4.27; N, 11.82; Br, 45.50.

EXAMPLE 31

3,4-Dibromo-N,N,α-trimethyl-5-propylpyrazole-1-acetamide and 4,5-dibromo-N,N,α-trimethyl-3-propylpyrazole-1-acetamide

Part A - 4,5-Dibromo-3-propylpyrazole

Following the procedure of Example 30, Part A, but substituting 3-propylpyrazole for 3-ethylpyrazole, there was prepared 4,5-dibromo-3-propylpyrazole having a melting point at 57.5° to 58° C.

Analysis: Calc'd. for $C_6H_8Br_2N_2$: C, 26.89; H, 3.01; N, 10.46; Br, 59.64. Found: C, 26.92; H, 3.10; N, 10.76; Br, 59.58.

Part B - 3,4-Dibromo-N,N,α-trimethyl-5-propylpyrazole-1-acetamide and 4,5-dibromo-N,N,α-trimethyl-3-propylpyrazole-1-acetamide Following the procedure of Example 30, Part B, but substituting the 4,5-dibromo-3-propylpyrazole prepared in Part A, above, for the 4,5-dibromo-3-ethyl-pyrazole, there was prepared 4,5-dibromo-N,N,α-trimethyl-3-propylpyrazole-1-acetamide having a melting point at 39° to 41° C.

Analysis: Calc'd. for $C_{11}H_{17}Br_2N_3O$: C, 35.99; H, 4.67; N, 11.45. Found: C, 36.24; H, 4.75; N, 11.37. and 3,4-dibromo-N,N,α-trimethyl-5-propylpyrazole-1-acetamide with a melting point at 100° to 101° C.

Analysis: Calc'd. for $C_{11}H_{17}Br_2N_3O$: C, 35.49; H, 4.67; N, 11.45. Found: C, 35.80; H, 4.60; N, 11.38.

EXAMPLE 32

3,4-Dibromo-5-isopropyl-N,N,α-trimethylpyrazole-1-acetamide and 4,5-dibromo-3-isopropyl-N,N,α-trimethylpyrazole-1-acetamide

Part A - 4,5-Dibromo-3-isopropylpyrazole

Following the procedure of Example 30, Part A, but substituting 3-isopropylpyrazole for 3-ethylpyrazole, there was prepared 4,5-dibromo-3-isopropylpyrazole having a melting point at 137° to 139° C.

Analysis: Calc'd. for $C_6H_8Br_2N_2$: C, 26.89; H, 3.01; N, 10.46; Br, 59.64. Found: C, 27.04; H, 3.05; N, 10.75; Br, 59.62.

Part B -
3,4-Dibromo-5-isopropyl-N,N,α-trimethylpyrazole-1-acetamide and
4,5-dibromo-3-isopropyl-N,N,α-trimethylpyrazole-1-acetamide Following the procedure of Example 30, Part B, but substituting the 4,5-dibromo-3-isopropylpyrazole prepared in Part A, above, for the 4,5-dibromo-3-ethylpyrazole, there was prepared 4,5-dibromo-3-isopropyl-N,N,α-trimethylpyrazole-1-acetamide which was a viscous oil which could not be crystallized.

Analysis: Calc'd. for $C_{11}H_{17}Br_2N_3O$: C, 35.99; H, 4.67; N, 11.45. Found: C, 36.20; H, 4.71; N, 11.49.
and 3,4-dibromo-5-isopropyl-N,N,α-trimethylpyrazole-1-acetamide having a melting point at 117.5° to 118° C.

Analysis: Calc'd. for $C_{11}H_{17}Br_2N_3O$: C, 35.99; H, 4.67; N, 11.45. Found: C, 36.21; H, 4.69; N, 11.46.

EXAMPLE 33

3,4-Dibromo-5-butyl-N,N,α-trimethylpyrazole-1-acetamide and
4,5-dibromo-3-butyl-N,N,α-trimethylpyrazole-1-acetamide Part A - 4,5-Dibromo-3-butylpyrazole Following the procedure of Example 30, Part A, but substituting 3-butylpyrazole for 3-ethylpyrazole, there was prepared 4,5-dibromo-3-butylpyrazole with a melting point at 51° to 52° C.

Analysis: Calc'd. for $C_7H_{10}Br_2N_2$: C, 29.81; H, 3.57; N, 9.94. Found: C, 30.03; H, 3.62; N, 10.02.

Part B -
3,4-Dibromo-5-butyl-N,N,α-trimethylpyrazole-1-acetamide and
4,5-dibromo-3-butyl-N,N,α-trimethylpyrazole-1-acetamide Following the procedure of Example 30, Part B, but substituting the 4,5-dibromo-3-butylpyrazole prepared in Part A, above, for the 4,5-dibromo-3-ethylpyrazole, there was prepared 4,5-dibromo-3-butyl-N,N,α-trimethylpyrazole-1-acetamide having a melting point at 40° to 44° C. This sample contained about 20% of the 5-butyl isomer.

Analysis: Calc'd. for $C_{12}H_{19}Br_2N_3O$: C, 37.81; H, 5.02; N, 11.03; Br, 41.94. Found: C, 37.98; H, 5.02; N, 10.96; Br, 42.03.
and 3,4-dibromo-5-butyl-5-butyl-N,N,α-trimethylpyrazole-1-acetamide having a melting point at 84.5° to 85° C.

Analysis: Calc'd. for $C_{12}H_{19}Br_2N_3O$: C, 37.81; H, 5.02; N, 11.03; Br, 41.94. Found: C, 37.75; H, 5.22; N, 10.99; Br, 41.96.

EXAMPLE 34

3,4-Dibromo-5-tert-butyl-N,N,α-trimethylpyrazole-1-acetamide

Part A - 4,5-Dibromo-3-tert-butylpyrazole

Following the procedure of Example 30, Part A, but substituting 3-tert-butylpyrazole for 3-ethylpyrazole, there was prepared 4,5-dibromo-3tert-butylpyrazole with a melting point at 224° to 227° C.

Analysis: Calc'd. for $C_7H_{10}Br_2N_2$: C, 29.81; H, 3.57; N, 9.94. Found: C, 30.06; H, 3.68; N, 10.01.

Part B -
3,4-Dibromo-5-tert-butyl-N,N,α-trimethylpyrazole-1-acetamide

Following the procedure of Example 30, Part B, but substituting the 4,5-dibromo-3-tert-butylpyrazole prepared in Part A, above, for the 4,5-dibromo-3-ethylpyrazole, there was prepared 3,4-dibromo-5-tert-butyl-N,N,α-trimethylpyrazole-1-acetamide having a melting point at 95° to 98° C.

Analysis: Calc'd. for $C_{12}H_{19}Br_2N_3O$: C, 37.81; H, 5.02; N, 11.03; Br, 41.94. Found: C, 37.96; H, 5.21; N, 10.90; Br, 41.91.

EXAMPLE 35

3,4-Dibromo-N,N,α,5-tetramethylpyrazole-1-acetamide and
4,5-dibromo-N,N,α,3-tetramethylpyrazole-1-acetamide Following the procedure of Example 30, Part B, but substituting the known 4,5-dibromo-3-methylpyrazole for the 4,5-dibromo-3-ethylpyrazole, there was prepared 4,5-dibromo-N,N,α,3-tetramethylpyrazole-1-acetamide having a melting point at 109° to 110° C.

Analysis: Calc'd. for $C_9H_{13}Br_2N_3O$: C, 31.88; H, 3.86; N, 12.40; Br, 47.14. Found: C, 31.96; H, 3.88; N, 12.68; Br, 46.92.
and 3,4-dibromo-N,N,α, 5-tetramethylpyrazole-1-acetamide having a melting point at 69° to 71° C.

Analysis: Calc'd. for $C_9H_{13}Br_2N_3O$: C, 31.88; H, 3.86; N, 12.40; Br, 47.14. Found: C, 31.82; H, 3.79; N, 12.52; Br, 46.89.

The preparation of the compounds in Example 35 was also described in Example 1, Part C.

EXAMPLE 36

4-Bromo-3-isopropyl-N,N,α-trimethylpyrazole-1-acetamide

Part A - 4-Bromo-3-isopropylpyrazole

To a stirred solution of sodium acetate (19.7 g., 0.24 mole) in acetic acid (100 ml.) and water (15 ml.), 3-isopropylpyrazole (11.0 g., 0.1 mole) was added, followed by dropwise addition of bromine (16.0 g., 0.11 mole) keeping the internal temperature below 15° C. The mixture was kept at 25° C. for 15 hours, treated with water (200 ml.) and extracted with ethyl ether (3 × 50 ml.), and the ether layer washed with water (1 × 50 ml.) dried, (sodium sulfate) and evaporated under reduced pressure. The resultant pale yellow oil was distilled to give 4-bromo-3-isopropylpyrazole (15.3 g., 81%) with a boiling point of 85° C. at 0.06 mm Hg.

Analysis: Calc'd. for $C_6H_9BrN_2$: C, 38.11; H, 4.80; N, 14.82; Br, 42.27. Found: C, 37.91; H, 4.89; N, 14.83; Br, 42.15.

Part B -
4-Bromo-3-isopropyl-N,N,α-trimethylpyrazole-1-acetamide

Sodium hydride (2.4 g., 0.06 mole) (57% oily dispersion) was washed with dry toluene (50 ml.) and then suspended in dry toluene (50 ml.). 4-Bromo-3-isopropylpyrazole (5.7 g., 0.03 mole) in toluene (10 ml.) was added drop by drop to the sodium hydride suspension, the mixture heated to reflux, and then treated dropwise with a solution of 2-chloro-N,N-dimethylpropionamide (8.1 g., 0.06 mole). Heating was continued for 4 hours, the mixture cooled, and treated with toluene (60 ml.) and water (40 ml.). The toluene layer was washed with water, (2 × 60 ml.), dried (magnesium sulfate) and the solvent removed under reduced pressure.

The resulting oil was distilled to yield 4-bromo-3-isopropyl-N,N,α-trimethylpyrazole-1-acetamide (5.7 g., 67%) with a boiling point of 99° to 101° C. at 0.03 mm Hg. On standing, the oil solidified to give crystals having a melting point at 63° to 65° C. The presence of 6% of 4-bromo-5-isopropyl-N,N,α-trimethylpyrazole-1-acetamide was apparent from the nuclear magnetic resonance spectrum.

Analysis: Calc'd. for $C_{11}H_{18}BrN_3O$: C, 45.84; H, 6.29; N, 14.58. Found: C, 45.92; H, 6.41; N, 14.60.

EXAMPLE 37

4-Bromo-3-ethyl-N,N,α-trimethylpyrazole-1-acetamide

Part A

Following the procedure of Example 36, Part A, but substituting 3-ethylpyrazole for 3-isopropylpyrazole, there was prepared 4-bromo-3-ethylpyrazole with a boiling point at 125° C. at 0.07 mm Hg.

Analysis: Calc'd. for $C_5H_7BrN_2$: C, 34.30; H, 4.02; N, 16.00. Found: C, 34.33; H, 4.04; N, 16.32.

Part B

Following the procedure of Example 36, Part B, but substituting 4-bromo-3-ethylpyrazole for 4-bromo-3-isopropylpyrazole, there was prepared 4-bromo-3-ethyl-N,N,α-trimethylpyrazole-1-acetamide with a boiling point at 99° to 100° C. at 0.05 mm Hg. About 25% of the 4-bromo-5-ethyl-N,N,α-trimethylpyrazole-1-acetamide isomer was present.

Analysis: Calc'd. for $C_{10}H_{16}BrN_3O$: C, 43.80; H, 5.88; N, 15.32. Found: C, 44.10; H, 6.09; N, 15.08.

EXAMPLE 38

4-Bromo-N,N,α-trimethyl-3-propylpyrazole-1-acetamide

Part A

Following the procedure of Example 36, Part A, but substituting 3-propylpyrazole for 3-isopropylpyrazole there was prepared 4-bromo-3-propylpyrazole with a melting point at 44° to 45° C.

Analysis: Calc'd. for $C_6H_9BrN_2$: C, 38.11; H, 4.80; N, 14.82; Br, 42.27. Found; C, 38.40; H, 4.95; N, 15.08; Br, 42.26.

Part B

Following the procedure of Example 36, Part B, but substituting 4-bromo-3-propylpyrazole for 4-bromo-3-isopropylpyrazole there was prepared 4-bromo-N,N,α-trimethyl-3-propylpyrazole-1-acetamine with a melting point at 67° to 69° C. About 22% of the 4-bromo-N,N,α-trimethyl-5-propylpyrazole-1-acetamide isomer was present.

Analysis: Calc'd. for $C_{11}H_{18}BrN_3O$: C, 45.84; H, 6.29; N, 14.58. Found: C, 46.13; H, 6.53; N, 14.81.

EXAMPLE 39

4-Bromo-3-butyl-N,N,α-trimethylpyrazole-1-acetamide

Part A

Following the procedure of Example 36, Part A, but substituting 3-butylpyrazole for 3-isopropylpyrazole, there was prepared 4-bromo-3-butylpyrazole with a boiling point at 95° at 0.06 mm Hg.

Analysis: Calc'd. for $C_7H_{11}BrN_2$: C, 41.39; H, 5.46; N, 13.85; Br, 39.35. Found: C, 41.28; H, 5.54; N, 13.85; Br, 39.15.

Part B

Following the procedure of Example 36, Part B, but substituting 4-bromo-3-butylpyrazole for 4-bromo-3-isopropylpyrazole there was prepared 4-bromo-3-butyl-N,N,α-trimethylpyrazole-1-acetamide having a melting point at 68° to 77° C. About 22% of the 4-bromo-5-butyl-N,N,α-trimethylpyrazole-1-acetamide isomer was present.

Analysis: Calc'd. for $C_{12}H_{20}BrN_3O$: C, 47.69; H, 6.67; N, 13.90. Found: C, 47.98; H, 6.79; N, 13.67.

EXAMPLE 40

4-Bromo-3-tert-butyl-N,N,α-trimethylpyrazole-1-acetamide

Part A

Following the procedure of Example 36, Part A, but substituting 3-tert-butylpyrazole for 3-isopropylpyrazole, there was prepared 4-bromo-3-tert-butylpyrazole having a melting point at 127° to 128° C.

Analysis: Calc'd. for $C_7H_{11}BrN_2$: C, 41.39; H, 5.46; N, 13.80. Found: C, 40.15; H, 5.46; N, 13.55.

Part B

Following the procedure of Example 36, Part B, but substituting 4-bromo-3-tert-butylpyrazole for 4-bromo-3-isopropylpyrazole there was prepared 4-bromo-3-tert-butyl-N,N,α-trimethylpyrazole-1-acetamide having a melting point at 94° to 96° C.

Analysis: Calc'd. for $C_{12}H_{20}BrN_3O$: C, 47.69; H, 6.67; N, 13.90. Found: C, 47.68; H, 6.54; N, 13.68.

EXAMPLE 41

4-Chloro-3-cyclohexyl-N,N,α-trimethylpyrazole-1-acetamide

Following the procedure of Example 36, Part B, but substituting 4-chloro-3-cyclohexylpyrazole for 4-bromo-3-isopropylpyrazole there was obtained 4-chloro-3-cyclohexyl-N,N,α-trimethylpyrazole-1-acetamide having a melting point at 111° to 113° C.

Analysis: Calc'd. for $C_{14}H_{22}ClN_3O$: C, 59.25; H, 7.81; N, 14.81; Cl, 12.49. Found: C, 59.54; H, 7.70; N, 14.98; Cl, 12.59.

EXAMPLE 42

4-Bromo-N,N,α,3-tetramethylpyrazole-1-acetamide
and
4-Bromo-N,N,α,5-tetramethylpyrazole-1-acetamide Following the procedure of Example 30, Part B, but substituting 4-bromo-3-methylpyrazole for 4,5-dibromo-3-ethylpyrazole, there was prepared 4-bromo-N,N,α,3-tetramethylpyrazole-1-acetamide with a melting point at 85° to 87° C.

Analysis: Calc'd. for $C_9H_{14}BrN_3O$: C, 41.55; H, 5.42; N, 16.15; Br, 30.72. Found: C, 41.63; H, 5.46; N, 15.98; Br, 30.67.

and 4-bromo-N,N,α,5-tetramethylpyrazole-1-acetamide having a melting point at 782° to 80° C.

Analysis: Calc'd. for $C_9H_{14}BrN_3O$: C, 41.55; H, 5.42; N, 16.15; Br, 30.72. Found: C, 41.63; H, 5.38; N, 16.23; Br, 30.52.

EXAMPLE 43

4-Chloro-3-cyclohexyl-N,N,α,α-tetramethylpyrazole-1-acetamide

Following the procedure of Example 26, Part B, but substituting 4-chloro-3-cyclohexyl-α,α-dimethylpyrazole-1-acetic acid for 3,4-dibromo-α,α,5-trimethylpyrazole-1-acetic acid there was prepared 4-chloro-3-cyclohexyl-N,N,α,α-tetramethylpyrazole-1-acetamide having a melting point at 133° to 134.5° C.

Analysis: Calc'd. for $C_{15}H_{24}ClN_3O$: C, 60.49; H, 8.12; N, 14.11; Cl, 11.91.

EXAMPLE 44

N,N,α,3-Tetramethylpyrazole-1-acetamide and N,N,α,5-tetramethylpyrazole-1-acetamide Following the procedure of Example 36, Part B, but substituting 3-methylpyrazole for 4-bromo-3-isopropylpyrazole, there was prepared N,N,α,3-tetramethylpyrazole-1-acetamide with a melting point at 42° to 55° C. About 22% of the N,N,α,5-tetramethylpyrazole-1-acetamide isomer was present.

Analysis: Calc'd. for $C_9H_{15}N_3O$: C, 59.64; H, 8.34; N, 23.18. Found: C, 58.83; H, 8.54; N, 21.50.

EXAMPLE 45

3-Ethyl-N,N,α-trimethylpyrazole-1-acetamide and 5-ethyl-N,N,α-trimethylpyrazole-1-acetamide Following the procedure of Example 36, Part B, but substituting 3-ethylpyrazole for 4-bromo-3-isopropylpyrazole, there was prepared 3-ethyl-N,N,α-trimethylpyrazole-1-acetamide having a boiling point at 88° to 90° C. at 0.3 mm Hg. About 20% of the 5-ethyl-N,N,α-trimethylpyrazole-1-acetamide isomer was present.

Analysis: Calc'd. for $C_{10}H_{17}N_3O$: C, 61.49; H, 8.77; N, 21.51. Found: C, 61.57; H, 8.83; N, 21.06.

EXAMPLE 46

N,N,α-trimethyl-3-propylpyrazole-1-acetamide and N,N,α-trimethyl-5-propylpyrazole-1-acetamide Following the procedure of Example 36, Part B, but substituting 3-propylpyrazole for 4-bromo-3-isopropylpyrazole, there was prepared N,N,α-trimethyl-3-propylpyrazole-1-acetamide having a boiling point at 144° C. at 0.02 mm Hg. About 20% of the N,N,α-trimethyl-5-propylpyrazole-1-acetamide isomer was present.

Analysis: Calc'd. for $C_{11}H_{19}N_3O$: C, 63.13; H, 9.15; N, 20.08. Found: C, 63.19; H, 9.17; N, 19.76.

EXAMPLE 47

3-Isopropyl-N,N,α-trimethylpyrazole-1-acetamide and 5-isopropyl-N,N,α-trimethylpyrazole-1-acetamide Following the procedure of Example 36, Part B, but substituting 3-isopropylpyrazole for 4-bromo-3-isopropylpyrazole, there was prepared 3-isopropyl-N,N,α-trimethylpyrazole-1-acetamide having a boiling point at 83° C. at 0.03 mm Hg. About 10% of the 5-isopropyl-N,N,α-trimethylpyrazole-1-acetamide isomer was present.

Analysis: Calc'd. for $C_{11}H_{19}N_3O$: C, 63.13; H, 9.15; N, 20.08. Found: C, 62.79; H, 9.31; N, 19.73.

EXAMPLE 48

3-Butyl-N,N,α-trimethylpyrazole-1-acetamide and 5-butyl-N,N,α-trimethylpyrazole-1-acetamide Following the procedure of Example 36, Part B, but substituting 3-butylpyrazole for 4-bromo-3-isopropylpyrazole, there was prepared 3-butyl-N,N,α-trimethylpyrazole-1-acetamide having a boiling point at 99° C. at 0.1 mm Hg. About 25% of the 5-butyl-N,N,α-trimethylpyrazole-1-acetamide isomer was present.

Analysis: Calc'd. for $C_{12}H_{21}N_3O$: C, 64.54; H, 9.48; N, 18.82. Found: C, 64.65; H, 9.90; N, 18.81.

EXAMPLE 49

3-Tert-butyl-N,N,α-trimethylpyrazole-1-acetamide

Following the procedure of Example 36, Part B, but substituting 3-tert-butylpyrazole for 4-bromo-3-isopropylpyrazole, there was prepared 3-tert-butyl-N,N,α-trimethylpyrazole-1-acetamide having a boiling point at 79° to 83° C. at 0.02 mm Hg.

Analysis: Calc'd. for $C_{12}H_{21}N_3O$: C, 64.54; H, 9.48; N, 18.82. Found: C, 64.84; H, 9.58; N, 18.70.

EXAMPLE 50

3-Cyclohexyl-N,N,α-trimethylpyrazole-1-acetamide

Following the procedure of Example 36, Part B, but substituting 3-cyclohexylpyrazole for 4-bromo-3-isopropylpyrazole, there was prepared 3-cyclohexyl-N,N,α-trimethylpyrazole-1-acetamide having a boiling point at 144° to 151° C. at 0.05 mm Hg.

Analysis: Calc'd. for $C_{14}H_{23}N_3O$: C, 67.43; H, 9.30; N, 16.85. Found: C, 67.22; H, 9.33; N, 16.69.

EXAMPLE 51

3-Cyclohexyl-N,N,α,α-tetramethylpyrazole-1-acetamide

Following the procedure of Example 26, Part B, but substituting 3-cyclohexyl-α,α-dimethylpyrazole-1-acetic acid for 3,4-dibromo-α,α,5-trimethylpyrazole-1-acetic acid, there was prepared 3-cyclohexyl-N,N,α,α-tetramethylpyrazole-1-acetamide having a melting point at 84.5° to 87° C.

Analysis: Calc'd. for $C_{15}H_{25}N_3O$: C, 68.40; H, 9.57; N, 15.96. Found: C, 68.41; H, 9.97; N, 16.09.

EXAMPLE 52

4-Bromo-N,N,α,3,5-pentamethylpyrazole-1-acetamide

Following the procedure of Example 36, Part B, but substituting 4-bromo-3,5-dimethylpyrazole for 4-bromo-3-isopropylpyrazole, there was prepared 4-bromo-N,N,α,3,5pentamethylpyrazole-1-acetamide having a boiling point at 125° C. at 0.07 mm Hg.

Analysis: Calc'd. for $C_{10}H_{16}BrN_3O$: C, 43.80; H, 5.88; N, 15.52. Found: C, 43.51; H, 5.94; N, 16.06.

EXAMPLE 53

4-Bromo-N,N,α,5-tetramethyl-3-(trifluoromethyl)-pyrazole-1-acetamide

Following the procedure of Example 36, Part B, but substituting 4-bromo-5-methyl-3-(trifluoromethyl)-pyrazole for 4-bromo-3-isopropylpyrazole, there was prepared 4-bromo-N,N,α,5-tetramethyl-3-(trifluoromethyl)pyrazole-1-acetamide, having a melting point of 86° to 88° C.

Analysis: Calc'd. for $C_{10}H_{13}BrF_3N_3O$: C, 36.60; H, 3.99; N, 12.80. Found: C, 36.80; H, 4.02; N, 12.81.

EXAMPLE 54

4-Bromo-3-isobutyl-N,N,α,5-tetramethylpyrazole-1-acetamide

Following the procedure of Example 36, Part B, but substituting 4-bromo-3-isobutyl-5-methylpyrazole for 4-bromo-3-isopropylpyrazole, there was prepared 4-bromo-3-isobutyl-N,N,α,5-tetramethylpyrazole-1-acetamide, having a boiling point at 132° C. at 0.03 mm Hg.

Analysis: Calc'd. for $C_{13}H_{22}BrN_3O$: C, 49.37; H, 7.01; N, 13.29; Br, 25.27. Found: C, 49.54; H, 7.41; N, 12.92; Br, 24.77.

EXAMPLE 55

4-Bromo-3,5-diethyl-N,N,α-trimethylpyrazole-1-acetamide

Following the procedure of Example 36, Part B, but substituting 4-bromo-3,5-diethylpyrazole for 4-bromo-3-isopropylpyrazole, there was prepared 4-bromo-3,5-diethyl-N,N,α-trimethylpyrazole-1-acetamide, having a boiling point at 105° C. at 0.02 mm Hg.

Analysis: Calc'd. for $C_{12}H_{20}BrN_3O$: C, 47.69; H, 6.67; N, 13.90. Found: C, 47.93; H, 7.02; N, 13.41.

EXAMPLE 56

4-Bromo-N,N,α-trimethyl-3,5-dipropylpyrazole-1-acetamide

Following the procedure of Example 36, Part B, but substituting 4-bromo-3,5-dipropylpyrazole for 4-bromo-3-isopropylpyrazole, there was prepared 4-bromo-N,N,α-trimethyl-3,5-dipropylpyrazole-1-acetamide having a boiling point at 128° C. at 0.05 mm Hg.

Analysis: Calc'd. for $C_{14}H_{24}BrN_3O$: C, 50.91; H, 7.32; N, 12.72; Br, 24.20. Found: C, 51.13; H, 7.32; N, 12.65; Br, 24.10.

EXAMPLE 57

Preparation of 4-Bromo-N-ethyl-N,α,3,5-tetramethylpyrazole-1-acetamide

Part A

Following the procedure of Example 1, Part A, but substituting 4-bromo-3,5-dimethylpyrazole for 4,5-dibromo-3-methylpyrazole, there was prepared 4-bromo-α,3,5-trimethylpyrazole-1-acetic acid, ethyl ester having a melting point at 57° to 57.5° C.

Analysis: Calc'd. for $C_{10}H_{15}BrN_2O_2$: C, 43.65; H, 5.49; N, 10.18. Found: C, 43.41; H, 5.43; N, 9.83.

Part B

Following the procedure of Example 1, Part B, but substituting the 4-bromo-α,3,5-trimethylpyrazole-1-acetic acid, ethyl ester prepared in Part A, above, for the 3,4-dibromo-α,5dimethylpyrazole-1-acetic acid, ethyl ester, there was prepared 4-bromo-α,3,5-trimethylpyrazole-1-acetic acid having a melting point at 134° to 135° C.

Analysis: Calc'd. for $C_8H_{11}BrN_2O_2$: C, 38.88; H, 4.49; N, 11.34. Found: C, 39.50; H, 4.44; N, 11.64.

Part C

Following the procedure of Example 1, Part C, but substituting the 4-bromo-α,3,5-trimethylpyrazole-1-acetic acid prepared in Part B, above, for 3,4-dibromo-α,5-dimethylpyrazole-1-acetic acid, and ethylmethylamine for dimethylamine there was prepared 4-bromo-N-ethyl-N,α,3,5-tetramethylpyrazole-1-acetamide having a melting point at 45° to 46.5° C.

Analysis: Calc'd. for $C_{11}H_{18}BrN_3O$: C, 45.84; H, 6.29; N, 14.58. Found: C, 45.67; H, 6.28; N, 14.58

EXAMPLE 58

4-Bromo-N,N-diethyl-α,3,5-trimethylpyrazole-1-acetamide

Following the procedure of Example 1, Part C, but substituting diethylamine for dimethylamine, and further substituting the 4-bromo-α,3,5-trimethylpyrazole-1-acetic acid prepared in Example 57, Part B, above, for 3,4-dibromo-α,5-dimethylpyrazole-1acetic acid, there was prepared the corresponding 4-bromo-N,N-diethyl-α,3,5-trimethylpyrazole-1-acetamide having a boiling point at 142° C. at 0.03 mm Hg.

Analysis: Calc'd. for $C_{12}H_{20}BrN_3O$: C, 47.69; H, 6.67; N, 13.90. Found: C, 47.71; H, 6.70; N, 13.74.

EXAMPLE 59

4-Bromo-α,3,5-trimethyl-N,N-dipropylpyrazole-1-acetamide

Following the procedure of Example 1, Part C, but substituting dipropylamine for dimethylamine, and further substituting the 4-bromo-α,3,5-trimethylpyrazole-1-acetic acid prepared in Example 57, Part B, above, for 3,4-dibromo-α,5-dimethylpyrazole-1-acetic acid, there was prepared the corresponding 4-bromo-α,3,5-trimethyl-N,N-dipropylpyrazole-1-acetamide having a boiling point at 124° C. at 0.03 mm Hg.

Analysis: Calc'd. for $C_{14}H_{24}BrN_3O$: C, 50.91; H, 7.32; N, 12.72. Found: C, 50.97; H, 7.26; N, 12.68.

EXAMPLE 60

Preparation of 4-Bromo-α-ethyl-N,N,3,5-tetramethylpyrazole-1-acetamide

Part A

Following the procedure of Example 1, Part A, but substituting ethyl 2-bromobutyrate for ethyl 2-bromopropionate and 4-bromo-3,5-dimethylpyrazole for 4,5-dibromo-3-methylpyrazole there was prepared 4-bromo-α-ethyl-3,5-dimethylpyrazole-1-acetic acid, ethyl ester as a brown oil which was not further purified.

Part B

Following the procedure of Example 1, Part B, but substituting the 4-bromo-α-ethyl-3,5-dimethylpyrazole-1-acetic acid, ethyl ester prepared in Part A, above, for 3,4-dibromo-α,5-dimethylpyrazole-1-acetic acid, ethyl ester, there was prepared 4-bromo-α-ethyl-3,5-dimethylpyrazole-1-acetic acid having a melting point at 109° to 111° C.

Analysis: Calc'd. for $C_9H_{13}BrN_2O_2$: C, 41.39; H, 5.02; N, 10.73; Br, 30.61. Found: C, 41.42; H, 5.17; N, 10.70; Br, 30.37.

Part C

Following the procedure of Example 1, Part C, but substituting the 4-bromo-α-ethyl-3,5-dimethylpyrazole-1-acetic acid prepared in Part B, above, for the 3,4-dibromo-α,5-dimethylpyrazole-1-acetic acid, there was prepared 4-bromo-α-ethyl-N,N,3,5-tetramethylpyrazole-1-acetamide having a melting point at 66.5° to 67.5° C.

Analysis: Calc'd. for $C_{11}H_{18}BrN_3O$: C, 45.84; H, 6.29; N, 14.58. Found: C, 45.96; H, 6.31; N, 14.62.

Example 61

4-Bromo-N,N,α-triethyl-3,5-dimethylpyrazole-1-acetamide

Following the procedure of Example 1, Part C, but substituting diethylamine for dimethylamine and further substituting the 4-bromo-α-ethyl-3,5-dimethylpyrazole-1-acetic acid prepared in Example 60, Part B, above, for the 3,4-dibromo-α,5-dimethylpyrazole-1-acetic acid, there was prepared the corresponding 4-bromo-N,Nα-triethyl-3,5-dimethylpyrazole-1-acetamide having a melting point at 42° to 44° C.

Analysis: Calc'd. for $C_{13}H_{22}BrN_3O$: C, 49.37; H, 7.01; N, 13.29. Found: C, 49.35; H, 6.92; N, 13.35.

EXAMPLE 62

N,N,α,3,5-Pentamethylpyrazole-1-acetamide

Following the procedure of Example 36, Part B, but substituting 3,5-dimethylpyrazole for 4-bromo-3-isopropylpyrazole, there was prepared N,N,α,3,5-pentamethylpyrazole-1-acetamide having a boiling point at 100° to 104° C. at 0.03 mm Hg.

Analysis: Calc'd. for $C_{10}H_{17}N_3O$: C, 61.51; H, 8.78; N, 21.52. Found: C, 61.73; H, 9.14; N, 21.18.

EXAMPLE 63

N,N,α,3,4-Pentamethylpyrazole-1-acetamide and N,N,α,4,5-pentamethylpyrazole-1-acetamide Following the procedure of Example 36, Part B, but substituting 3,4-dimethylpyrazole for 4-bromo-3-isopropylpyrazole, there was prepared N,N,α,3,4-pentamethylpyrazole-1-acetamide having a boiling point at 77° C. at 0.03 mm Hg. About 25% of the N,N,α,4,5pentamethylpyrazole-1-acetamide isomer was present.

Analysis: Calc'd. for $C_{10}H_{17}N_3O$: C, 61.51; H, 8.78; N, 21.52. Found: C, 61.20; H, 8.91; N, 21.05.

EXAMPLE 64

4-Ethyl-N,N,α,3-tetramethylpyrazole-1-acetamide and 4-ethyl-N,N,α,5-tetramethylpyrazole-1-acetamide Following the procedure of Example 36, Part B, but substituting 4-ethyl-3-methylpyrazole for 4-bromo-3-isopropylpyrazole, there was prepared 4-ethyl-N,N,α,3tetramethylpyrazole-1-acetamide having a boiling point at 97° C. at 0.25 mm Hg. About 30% of the 4-ethyl-N,N,α,5-tetramethylpyrazole-1-acetamide isomer was present.

Analysis: Calc'd. for $C_{11}H_{19}N_3O$: C, 63.13; H, 9.15; N, 20.08. Found: C, 62.88; H, 9.26; N, 19.88.

EXAMPLE 65

N,N,α,3,4,5-Hexamethylpyrazole-1-acetamide

Following the procedure of Example 36, Part B, but substituting 3,4,5-trimethylpyrazole for 4-bromo-3-isopropylpyrazole, there was prepared N,N,α,3,4,5-hexamethylpyrazole-1-acetamide having a melting point at 63° to 66° C.

Analysis: Calc'd. for $C_{11}H_{19}N_3O$: C, 63.13; H, 9.15; N, 20.08. Found: C, 63.02; H, 9.34; N, 19.82.

EXAMPLE 66

3-Cyclohexyl-N,N,α,4-tetramethylpyrazole-1-acetamide

Following the procedure of Example 36, Part B, but substituting 3-cyclohexyl-4-methylpyrazole for 4-bromo-3-isopropylpyrazole, there was prepared 3-cyclohexyl-N,N,α,4-tetramethylpyrazole-1-acetamide with a melting point at 96° to 98° C.

Analysis: Calc'd. for $C_{15}H_{25}N_3O$: C, 68.40; H, 9.57; N, 15.96. Found: C, 68.46; H, 9.80; N, 15.94.

EXAMPLE 67

3-Cyclohexyl-N,N,α,α,4-pentamethylpyrazole-1-acetamide

Following the procedure of Example 26, Part B, but substituting 3-cyclohexyl-α,α,4-trimethylpyrazole-1-acetic acid for 3,4-dibromo-α,α,5-trimethylpyrazole-1-acetic acid, there was prepared 3-cyclohexyl-N,N,α,α,4-pentamethylpyrazole-1-acetamide having a melting point at 87° to 89° C.

Analysis: Calc'd. for $C_{16}H_{27}N_3O$: C, 69.27; H, 9.81; N, 15.15. Found: C, 69.19; H, 10.07; N, 15.01.

EXAMPLE 68

Preparation of 3,4-Dibromo-N,N,α,5-tetramethylthiopyrazole-1-acetamide

A solution of 3,4-dibromo-N,N,α,5-tetramethylpyrazole-1-acetamide (6.78 g., 0.02 mole) in pyridine (30 ml.) was treated with phosphorous pentasulfide (6.66 g., 0.03 mole) and heated to reflux while the mixture was stirred vigorously. Heating was continued for 2 hours, the reaction mixture cooled, poured into ice water and filtered. After drying, the solid was chromatographed on a column of silica gel using ethyl acetate as the eluate. The white solid thus obtained was recrystallized from ethyl acetate to yield 3,4-dibromo-N,N,α,5-tetramethylthiopyrazole-1-acetamide having a melting point at 159° to 161° C.

Analysis: Calc'd. for $C_9H_{13}Br_2N_3S$: C, 30.44; H, 3.69; N, 11.83; S, 9.03; Br, 45.00. Found: C, 30.51; H, 3.78; N, 11.89; S, 9.14; Br, 45.01.

EXAMPLE 69

3,5-Dibromo-N,N-diethyl-α,4-dimethylthiopyrazole-1-acetamide

Following the procedure of Example 68, but substituting 3,5-dibromo-N,N-diethyl-α,4-dimethylpyrazole-1-acetamide for 3,4-dibromo-N,N,α,5-tetramethylpyrazole-1-acetamide there was prepared the corresponding 3,5-dibromo-N,N-diethylα,4-dimethylthiopyrazole-1-acetamide having a melting point at 189° to 191° C.

Analysis: Calc'd. for $C_{11}H_{17}Br_2N_3S$: C, 34.48; H, 4.47; N, 10.97. Found: C, 34.26; H, 4.41; N, 10.98.

EXAMPLE 70

4-Bromo-3-butyl-N,N,α-trimethylthiopyrazole-1-acetamide

Following the procedure of Example 68, but substituting 4-bromo-3-butyl-N,N,α-trimethylpyrazole-1- acetamide for 3,4-dibromo-N,N,α,5-tetramethylpyrazole-1-acetamide there was prepared 4-bromo-3-butyl-N,N,α-trimethylthiopyrazole-1-acetamide having a melting point at 37° to 39° C.

Analysis: Calc'd. for $C_{12}H_{20}BrN_3S$: C, 45.28; H, 6.33; N, 13.20. Found: C, 45.00; H, 6.40; N, 13.18.

EXAMPLE 71

4-Bromo-N,N,α,3,5-pentamethylthiopyrazole-1-acetamide Following the procedure of Example 68, but substituting 4-bromo-N,N,α,3,5-pentamethylpyrazole-1-acetamide for 3,4-dibromo-N,N,α,5-tetramethylpyrazole-1-acetamide there was prepared 4-bromo-N,N,α,3,5-pentamethylthiopyrazole-1-acetamide having a melting point at 119.5° to 121° C.

Analysis: Calc'd. for $C_{10}H_{16}BrN_3S$: C, 41.38; H, 5.56; N, 14.48. Found: C, 41.69; H, 5.77; N, 14.48.

EXAMPLE 72

4-Bromo-3-isopropyl-N,N,α-trimethylthiopyrazole-1-acetamide

Following the procedure of Example 68, but substituting 4-bromo-3-isopropyl-N,N,α-trimethylpyrazole-1-acetamide for 3,4-dibromo-N,N,α,5-tetramethylpyrazole-1-acetamide there was prepared 4-bromo-3-isopropyl-N,N,α-trimethylthiopyrazole-1-acetamide having a melting point at 85° to 87° C.

Analysis: Calc'd. for $C_{11}H_{18}BrN_3S$: C, 43.42; H, 5.96; N, 13.81. Found: C, 43.56; H, 5.99; N, 13.80.

EXAMPLE 73

4-Ethyl-N,N,α,3-tetramethylthiopyrazole-1-acetamide and 4-ethyl-N,N,α,5-tetramethylthiopyrazole-1-acetamide Following the procedure of Example 68, but substituting a 70:30 mixture of 4-ethyl-N,N,α,3-tetramethylpyrazole-1-acetamide and 4-ethyl-N,N,α,5-tetramethylpyrazole-1-acetamide for 3,4-dibromo-N,N,α,5-tetramethylpyrazole-1-acetamide there was prepared and separated by column chromatography (ethyl acetate as the eluent) 4-ethyl-N,N,α,3-tetramethylthiopyrazole-1-acetamide having a melting point at 65° to 67°C.

Analysis: Calc'd. for $C_{11}H_{19}N_3S$: C, 58.62; H, 8.50; N, 18.65. Found: C, 58.44; H, 8.32; N, 18.94.
and 4-ethyl-N,N,α,5-tetramethylthiopyrazole-1-acetamide having a melting point at 54° to 56° C.

Analysis: Calc'd. for $C_{11}H_{19}N_3S$: C, 58.62; H, 8.50; N, 18.65. Found: 58.46; H, 8.54; N, 18.48.

EXAMPLE 74

Following the procedure of the preceding Examples 68 through 73, inclusive, and substituting each of the compounds prepared in Examples 1 through 67, inclusive, there was prepared the corresponding thiopyrazole-1-acetamide.

EXAMPLE 75

A dispersible powder concentrate having the following percentage composition:

| | |
|---|---|
| 3,4-dibromo-N,N,α,5-tetramethylpyrazole-1-acetamide | 45.8% |
| Polymerized sodium salt of substituted benzoid long-chain sulfonic acid (Daxad 27) | 9.2% |
| Kaolinite | 45.0% | was prepared by mixing 250 g. of 3,4-dibromo-N,N,α,5tetramethylpyrazole-1acetamide, 50 g. of a polymerized sodium salt of substituted benzoid long-chain sulfonic acid (Daxad 27), and 245 g. of kaolinite. The mixture was milled to a particle size averaging 5 to 30 microns. It was suspended in 10 gals. of water, giving an aqueous spray containing about 6500 parts per million of active ingredient.

EXAMPLE 76

A fine granular formulation having the following percentage composition:

| | |
|---|---|
| 3,4-dibromo-N,N,α,5-tetramethylpyrazole-1-acetamide | 3.7% |
| Vermiculite (30/60 mesh) | 96.3% | was prepared by spraying a solution of 220 g. of 3,4-dibromo-N,N,α,5-tetramethylpyrazole-1-acetamide in 1000 ml. of methylene chloride onto 5780 g. of vermiculite (30 to 60 mesh) while the vermiculite was being tumbled and stirred so as to assure even distribution. The methylene chloride was then evaporated, leaving the active compound adsorbed on the vermiculite, and the vermiculite was pulverized.

EXAMPLE 77

An emulsifiable concentrate having the following percentage composition:

| | |
|---|---|
| 3,4-dibromo-N,N,α,5-tetramethylpyrazole-1-acetamide | 15.0% |
| Technical alkyl naphthalene boiling at 238° to 293° C. (Velsicol AR50) | 19.7% |
| Xylene | 17.4% |
| Acetone | 17.4% |
| Ethylene dichloride | 25.4% |
| Blend of alkyl aryl sulfonates and alkylphenoxy polyethoxy ethanols (Triton X-151) | 5.1% | was prepared by mixing 15.0 lbs. of 3,4-dibromo-N,N,α,5-tetramethylpyrazole-1-acetamide, 19.7 lbs. of Velsicol AR50, 17.4 lbs. of xylene, 17.4 lbs. of acetone, 25.4 lbs. of ethylene dichloride, and 5.1 lbs. of Triton X-151.

6.67 Lbs. of the concentrate mixed with 10 gals. of water gave a spray emulsion containing about 11,000 ppm of active ingredient.

EXAMPLE 78

An emulsifiable concentrate having the following percentage composition:

| | |
|---|---|
| 3,4-dibromo-N,N,α,5-tetramethylpyrazole-1-acetamide | 40.0% |
| Technical alkyl naphthalene boiling at 238° to 293° C. (Velsicol AR50) | 13.7% |
| Xylene | 12.3% |
| Acetone | 11.3% |
| Ethylene dichloride | 17.7% |
| Blend of alkyl aryl sulfonates and alkylphenoxy polyethoxy ethanol (Triton X-151) | 5.0% | was prepared by mixing 40.0 lbs. of 3,4-dibromo-N,N,α,5-tetramethylpyrazole-1-acetamide, 13.7 lbs. of Velsicol AR50, 12.3 lbs. of xylene, 11.3 lbs. of acetone, 17.7 lbs. of ethylene dichloride, and 5.0 lbs. of Triton X-151.

1.67 Lbs. of the concentrate mixed with 10 gals. of water gave a spray emulsion containing about 8,000 ppm of active ingredient.

EXAMPLE 79

A dispersible powder concentrate having the following percentage composition:

| | |
|---|---|
| 3,4-dibromo-N,N,$\alpha$,5-tetra-methylpyrazole-1-acetamide | 50% |
| Kaolinite clay (finely divided) | 46% |
| Sodium salt of condensed mono-naphthalene sulfonic acid (Lomar D) | 4% | was prepared by mixing 50 g. of 3,4-dibromo-N,N,$\alpha$,5-tetramethylpyrazole-1-acetamide, 46 g. of the kaolinite clay, and 4 g. of Lomar D. The mixture was milled to an average particle size of 5 to 30 microns.

EXAMPLE 80

A granular formulation having the following percentage composition:

| | |
|---|---|
| 3,4-dibromo-N,N,$\alpha$,5-tetra-methylpyrazole-1-acetamide | 1% |
| Pyrophyllite (30/60 mesh) | 99% | was prepared by dissolving 1.0 lb. of the 3,4-dibromo-N,N,$\alpha$,5-tetramethylpyrazole-1-acetamide in 10.0 l. of ethylene dichloride and spraying the solution on 99.0 lbs. of pyrophyllite. The granules were dried and then packaged for use.

EXAMPLE 81

Following the procedure of the preceding Examples 75 through 80, inclusive, compositions are similarly prepared substituting each of the compounds prepared in Example 2 through 74, inclusive, for the 3,4-dibromo-N,N,$\alpha$,5-tetramethylpyrazole-1-acetamide.

I claim:

1. A compound of the formula:

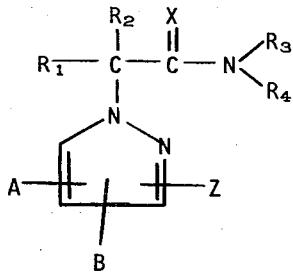

wherein $R_1$ and $R_2$ are the same or different and are hydrogen, alkyl of from 1 to 6 carbon atoms, inclusive, or phenyl; $R_3$ is hydrogen, alkyl of from 1 to 8 carbon atoms, inclusive, phenyl, or benzyl; $R_4$ is hydrogen or alkyl of from 1 to 6 carbon atoms, inclusive, and $R_3$ and $R_4$ can be joined together to form a heterocyclic ring selected from the group consisting of morpholine, pyrrolidine or piperidine; X is oxygen or sulfur; A and B are the same or different, and are hydrogen, alkyl of from 1 to 6 carbon atoms, inclusive, cycloalkyl of from 3 to 7 carbon atoms, inclusive, haloalkyl and halogen; Z is an alkyl group of from 1 to 6 carbon atoms, inclusive, or a cycloalkyl group of from 3 to 7 carbon atoms provided that when A and B are halogen, Z is located at the 4 or 5 positions.

2. A compound according to claim 1 which is 3,4-dibromo-N,N,$\alpha$,5-tetramethylpyrazole-1-acetamide.

3. A compound according to claim 1 which is 3,4-dibromo-N-ethyl-N,$\alpha$,5-trimethylpyrazole-1-acetamide.

4. A compound according to claim 1 which is 3,4-dibromo-N-isopropyl-N,$\alpha$,5-trimethylpyrazole-1-acetamide.

5. A compound according to claim 1 which is 3,4-dibromo-N-benzyl-N,$\alpha$,5-trimethylpyrazole-1-acetamide.

6. A compound according to claim 1 which is 3,4-dibromo-N,N-diethyl-$\alpha$,5-dimethylpyrazole-1-acetamide.

7. A compound according to claim 1 which is 3,4-dibromo-N-ethyl-N-isopropyl-$\alpha$,5-dimethylpyrazole-1-acetamide.

8. A compound according to claim 1 which is 3,4-dibromo-N,N-di-n-propyl-$\alpha$,5-dimethylpyrazole-1-acetamide.

9. A compound according to claim 1 which is 3,4-dibromo-N,N-diallyl-$\alpha$,5-dimethylpyrazole-1-acetamide.

10. A compound according to claim 1 which is 1-[2-(3,4-dibromo-5-methylpyrazol-1-yl)propionyl]pyrrolidine.

11. A compound according to claim 1 which is 4-[2-(3,4-dibromo-5-methylpyrazol-1-yl)propionyl]morpholine.

12. A compound according to claim 1 which is 3,4-dibromo-$\alpha$,5-dimethyl-N,N-diphenylpyrazole-1-acetamide.

13. A compound according to claim 1 which is 3,4-dibromo-N,$\alpha$,5-trimethylpyrazole-1-acetamide.

14. A compound according to claim 1 which is 3,4-dibromo-N-allyl-$\alpha$,5-dimethylpyrazole-1-acetamide.

15. A compound according to claim 1 which is 3,4-dibromo-N-cyclohexyl-$\alpha$,5-dimethylpyrazole-1-acetamide.

16. A compound according to claim 1 which is 3,4-dibromo-$\alpha$,5-dimethylpyrazole-1-acetanilide.

17. A compound according to claim 1 which is 3,4-dibromo-3',4'-dichloro-$\alpha$,5-dimethylpyrazole-1-acetanilide.

18. A compound according to claim 1 which is 3,4-dibromo-N,N,5-trimethylpyrazole-1-acetamide.

19. A compound according to claim 1 which is 3,4-dibromo-N,5-dimethylpyrazole-1-acetamide.

20. A compound according to claim 1 which is 3,4-dibromo-N-ethyl-N,5-dimethylpyrazole-1-acetamide.

21. A compound according to claim 1 which is 3,4-dibromo-N,N-diethyl-5-methylpyrazole-1-acetamide.

22. A compound according to claim 1 which is 3,4-dibromo-5-methyl-N,N-di-n-propylpyrazole-1-acetamide.

23. A compound according to claim 1 which is 3,4-dibromo-$\alpha$-ethyl-N,N,5-trimethylpyrazole-1-acetamide.

24. A compound according to claim 1 which is 3,4-dibromo-$\alpha$,N-diethyl-N,5-dimethylpyrazole-1-acetamide.

25. A compound according to claim 1 which is 3,4-dibromo-N,N,$\alpha$-triethyl-5-methylpyrazole-1-acetamide.

26. A compound according to claim 1 which is 3,4-dibromo-N,N,5-trimethyl-α-phenylpyrazole-1-acetamide.

27. A compound according to claim 1 which is 3,4-dibromo-N,N,α,α,5-pentamethylpyrazole-1-acetamide.

28. A compound according to claim 1 which is 3,5-dibromo-N,N,α,4-tetramethylpyrazole-1-acetamide.

29. A compound according to claim 1 which is 3,5-dibromo-N,N-diethyl-α,4-dimethylpyrazole-1-acetamide.

30. A compound according to claim 1 which is 3,5-dibromo-N,N-diethyl-4-methylpyrazole-1-acetamide.

31. A compound according to claim 1 which is 3,4-dibromo-5-ethyl-N,N,α-trimethylpyrazole-1-acetamide.

32. A compound according to claim 1 which is 3,4-dibromo-N,N,α-trimethyl-5-propylpyrazole-1-acetamide.

33. A compound according to claim 1 which is 3,4-dibromo-5-isopropyl-N,N,α-trimethylpyrazole-1-acetamide.

34. A compound according to claim 1 which is 3,4-dibromo-5-isopropyl-N,N,α-trimethylpyrazole-1-acetamide.

35. A compound according to claim 1 which is 3,4-dibromo-5-butyl-N,N,α-trimethylpyrazole-1-acetamide.

36. A compound according to claim 1 which is 3,4-dibromo-5-tert-butyl-N,N,α-trimethylpyrazole-1-acetamide.

37. A compound according to claim 1 which is 3,4-dibromo-N,N,α,5-tetramethylpyrazole-1-acetamide.

38. A compound according to claim 1 which is 4-bromo-3-isopropyl-N,N,α-trimethylpyrazole-1-acetamide.

39. A compound according to claim 1 which is 4-bromo-3-ethyl-N,N,α-trimethylpyrazole-1-acetamide.

40. A compound according to claim 1 which is 4-bromo-N,N,α-trimethyl-3-propylpyrazole-1-acetamide.

41. A compound according to claim 1 which is 4-bromo-3-butyl-N,N,α-trimethylpyrazole-1-acetamide.

42. A compound according to claim 1 which is 4-bromo-3-tert-butyl-N,N,α-trimethylpyrazole-1-acetamide.

43. A compound according to claim 1 which is 4-chloro-3-cyclohexyl-N,N,α-trimethylpyrazole-1-acetamide.

44. A compound according to claim 1 which is 4-bromo-N,N,α,3-tetramethylpyrazole-1-acetamide.

45. A compound according to claim 1 which is 4-bromo-N,N,α,5-tetramethylpyrazole-1-acetamide.

46. A compound according to claim 1 which is 4-chloro-3-cyclohexyl-N,N,α,α-tetramethylpyrazole-1-acetamide.

47. A compound according to claim 1 which is N,N,α,3-tetramethylpyrazole-1-acetamide.

48. A compound according to claim 1 which is N,N,α,5-tetramethylpyrazole-1-acetamide.

49. A compound according to claim 1 which is 3-ethyl-N,N,α-trimethylpyrazole-1-acetamide.

50. A compound according to claim 1 which is 5-ethyl-N,N,α-trimethylpyrazole-1-acetamide.

51. A compound according to claim 1 which is N,N,α-trimethyl-3-propylpyrazole-1-acetamide.

52. A compound according to claim 1 which is N,N,α-trimethyl-5-propylpyrazole-1-acetamide.

53. A compound according to claim 1 which is 3-isopropyl-N,N,α-trimethylpyrazole-1-acetamide.

54. A compound according to claim 1 which is 5-isopropyl-N,N,α-trimethylpyrazole-1-acetamide.

55. A compound according to claim 1 which is 3-butyl-N,N,α-trimethylpyrazole-1-acetamide.

56. A compound according to claim 1 which is 5-butyl-N,N,α-trimethylpyrazole-1-acetamide.

57. A compound according to claim 1 which is 3-tert-butyl-N,N,α-trimethylpyrazole-1-acetamide.

58. A compound according to claim 1 which is 3-cyclohexyl-N,N,α-trimethylpyrazole-1-acetamide.

59. A compound according to claim 1 which is 3-cyclohexyl-N,N,α,α-tetramethylpyrazole-1-acetamide.

60. A compound according to claim 1 which is 4-bromo-N,N,α,3,5-pentamethylpyrazole-1-acetamide.

61. A compound according to claim 1 which is 4-bromo-N,N,α,5-tetramethyl-3-(trifluoromethyl)-pyrazole-1-acetamide.

62. A compound according to claim 1 which is 4-bromo-3-isobutyl N,N,α,5-tetramethylpyrazole-1-acetamide.

63. A compound according to claim 1 which is 4-bromo-3,5-diethyl-N,N,α-trimethylpyrazole-1-acetamide.

64. A compound according to claim 1 which is 4-bromo-3,5-diethyl-N,N,α-trimethylpyrazole-1-acetamide.

65. A compound according to claim 1 which is 4-bromo-N,N,α-trimethyl-3,5-dipropylpyrazole-1-acetamide.

66. A compound according to claim 1 which is 4-bromo-N-ethyl-N,α,3,5-tetramethylpyrazole-1-acetamide.

67. A compound according to claim 1 which is 4-bromo-N,N,-diethyl-α,3,5-trimethylpyrazole-1-acetamide.

68. A compound according to claim 1 which is 4-bromo-α,3,5-trimethyl-N,N-dipropylpyrazole-1-acetamide.

69. A compound according to claim 1 which is 4-bromo-α-ethyl-N,N,3,5-tetramethylpyrazole-1-acetamide.

70. A compound according to claim 1 which is 4-bromo-N,N,α-triethyl-3,5-dimethylpyrazole-1-acetamide.

71. A compound according to claim 1 which is N,N,α,3,5-pentamethylpyrazole-1-acetamide.

72. A compound according to claim 1 which is N,N,α,3,4-pentamethylpyrazole-1-acetamide.

73. A compound according to claim 1 which is N,N,α,4,5-pentamethylpyrazole-1-acetamide.

74. A compound according to claim 1 which is 4-ethyl-N,N,α,3-tetramethylpyrazole-1-acetamide.

75. A compound according to claim 1 which is 4-ethyl-N,N,α,5-tetramethylpyrazole-1-acetamide.

76. A compound according to claim 1 which is N,N,α,3,4,5-hexamethylpyrazole-1-acetamide.

77. A compound according to claim 1 which is 3-cyclohexyl-N,N,α,4-tetramethylpyrazole-1-acetamide.

78. A compound according to claim 1 which is 3-cyclohexyl-N,N,α,α,4-pentamethylpyrazole-1-acetamide.

79. A compound according to claim 1 which is 3,4-dibromo-N,N,α,5-tetramethylthiopyrazole-1-acetamide.

80. A compound according to claim 1 which is 3,5-dibromo-N,N-diethyl-α,4-dimethylthiopyrazole-1-acetamide.

81. A compound according to claim 1 which is 4-bromo-3-butyl-N,N,α-trimethylthiopyrazole-1-acetamide.

82. A compound according to claim 1 which is 4-bromo-N,N,α,3,5-pentamethylthiopyrazole-1-acetamide.

83. A compound according to claim 1 which is 4-bromo-3-isopropyl-N,N,α-trimethylthiopyrazole-1-acetamide.

84. A compound according to claim 1 which is 4-ethyl-N,N,α,3-tetramethylthiopyrazole-1-acetamide.

85. A compound according to claim 1 which is 4-ethyl-N,N,α,5-tetramethylthiopyrazole-1-acetamide.

86. A method for controlling weeds or undesirable vegetation which comprises applying to the locus thereof a herbicidally effective amount of a compound of the formula:

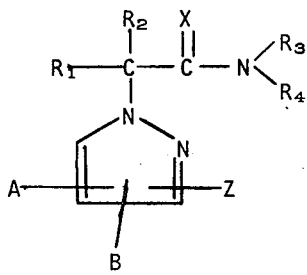

wherein $R_1$ and $R_2$ are the same or different and are hydrogen, alkyl of from 1 to 6 carbon atoms, inclusive, or phenyl; $R_3$ is hydrogen, alkyl of from 1 to 8 carbon atoms, inclusive, phenyl, or benzyl; $R_4$ is hydrogen or alkyl of from 1 to 6 carbon atoms, inclusive, and $R_3$ and $R_4$ can be joined together to form a heterocyclic ring selected from the group consisting of morpholine, pyrrolidine or piperidine; X is oxygen or sulfur; A and B are the same or different, and are hydrogen, alkyl of from 1 to 6 carbon atoms, inclusive, cycloalkyl of from 3 to 7 carbon atoms, inclusive, haloalkyl and halogen; Z is an alkyl group of from 1 to 6 carbon atoms, inclusive, or a cycloalkyl group of from 3 to 7 carbon atoms provided that when A and B are halogen, Z is located at the 4 or 5 positions.

87. A composition for herbicidal use comprising an inert adjuvant and, as the active ingredient, an effective amount of a compound of the formula:

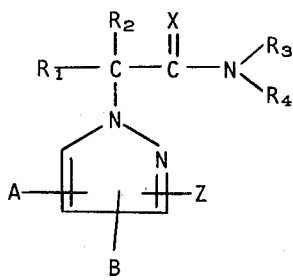

wherein $R_1$ and $R_2$ are the same or different and are hydrogen, alkyl of from 1 to 6 carbon atoms, inclusive, or phenyl; $R_3$ is hydrogen, alkyl of from 1 to 8 carbon atoms, inclusive, phenyl, or benzyl; $R_4$ is hydrogen or alkyl of from 1 to 6 carbon atoms, inclusive, and $R_3$ and $R_4$ can be joined together to form a heterocyclic ring selected from the group consisting of morpholine, pyrrolidine or piperidine; X is oxygen or sulfur; A and B are the same or different, and are hydrogen, alkyl of from 1 to 6 carbon atoms, inclusive, cycloalkyl of from 3 7 carbon atoms, inclusive, haloalkyl, and halogen; Z is an alkyl group of from 1 to 6 carbon atoms, inclusive, or a cycloalkyl group of from 3 to 7 carbon atoms provided that when A and B are halogen, Z is located at the 4 or 5 positions.

* * * * *